(12) United States Patent
Lai

(10) Patent No.: US 6,210,401 B1
(45) Date of Patent: *Apr. 3, 2001

(54) METHOD OF, AND APPARATUS FOR, SURGERY OF THE CORNEA

(76) Inventor: Shui T. Lai, 1223 Orchard Glen Cir., Encinitas, CA (US) 92024

( * ) Notice: Subject to any disclaimer, the term of this patent is extended or adjusted under 35 U.S.C. 154(b) by 0 days.

This patent is subject to a terminal disclaimer.

(21) Appl. No.: 09/130,547

(22) Filed: Aug. 6, 1998

Related U.S. Application Data

(63) Continuation of application No. 07/788,424, filed on Nov. 6, 1991, now abandoned, which is a continuation-in-part of application No. 07/740,004, filed on Aug. 2, 1991, now Pat. No. 5,280,491.

(51) Int. Cl.⁷ .................................................. A61B 18/18
(52) U.S. Cl. .................................. 606/12; 606/10; 606/4; 351/209
(58) Field of Search .............................. 606/4–6, 10–12; 351/209, 211

(56) References Cited

U.S. PATENT DOCUMENTS

| | | |
|---|---|---|
| 3,629,602 | 12/1971 | Firester . |
| 4,309,998 | 1/1982 | Aron nee Rosa et al. . |
| 4,583,539 | 4/1986 | Karlin et al. . |
| 4,630,274 | 12/1986 | Schafer . |
| 4,638,801 | 1/1987 | Daly et al. . |
| 4,648,400 | 3/1987 | Schneider et al. . |
| 4,648,892 | 3/1987 | Kittrell et al. . |
| 4,718,416 | 1/1988 | Nanaumi . |
| 4,721,379 | 1/1988 | L-Esperance . |
| 4,724,522 | 2/1988 | Belgorod . |
| 4,764,930 | 8/1988 | Bille et al. . |

(List continued on next page.)

FOREIGN PATENT DOCUMENTS

| | | |
|---|---|---|
| 3532464 | 3/1986 | (DE) . |
| 3532-464 | 3/1987 | (DE) . |
| 015186982 | 6/1985 | (EP) . |
| 296-982 | 12/1988 | (EP) . |
| 296982 | 12/1988 | (EP) . |

(List continued on next page.)

*Primary Examiner*—Michael Peffley
(74) *Attorney, Agent, or Firm*—Baker & Maxham; Freling E. Baker

(57) ABSTRACT

A laser-based method and apparatus for corneal surgery. The present invention is intended to be applied primarily to ablate organic materials, and human cornea in particular. The invention uses a laser source which has the characteristics of providing a shallow ablation depth (0.2 microns or less per laser pulse), and a low ablation energy density threshold (less than or equal to about 10 mJ/cm²), to achieve optically smooth ablated corneal surfaces. The preferred laser includes a laser emitting approximately 100–50,000 laser pulses per second, with a wave-length of about 198–300 nm and a pulse duration of about 1–5,000 picoseconds. Each laser pulse is directed by a highly controllable laser scanning system. Described is a method of distributing laser pulses and the energy deposited on a target surface such that surface roughness is controlled within a specific range. Included is a laser beam intensity monitor and a beam intensity adjustment means, such that constant energy level is maintained throughout an operation. Eye movement during an operation is corrected for by a corresponding compensation in the location of the surgical beam. Beam operation is terminated if the laser parameters or the eye positioning is outside of a predetermined tolerable range. The surgical system can be used to perform surgical procedures including removal of corneal scar, making incisions, cornea transplants, and to correct myopia, hyperopia, astigmatism, and other corneal surface profile defects.

10 Claims, 20 Drawing Sheets

U.S. PATENT DOCUMENTS

| | | |
|---|---|---|
| 4,784,135 | 11/1988 | Blum et al. . |
| 4,848,340 * | 7/1989 | Bille et al. .............................. 606/4 |
| 4,856,513 | 8/1989 | Muller . |
| 4,887,592 | 12/1989 | Loertscher . |
| 4,901,718 | 2/1990 | Bille et al. . |
| 4,907,586 | 3/1990 | Bille et al. . |
| 4,911,711 | 3/1990 | Telfair et al. . |
| 4,913,142 | 4/1990 | Kittrell et al. . |
| 4,941,093 | 7/1990 | Marshall et al. . |
| 4,973,330 | 11/1990 | Azema et al. . |
| 4,976,709 | 12/1990 | Sand . |
| 5,062,702 | 11/1991 | Bille . |
| 5,098,426 | 3/1992 | Sklar et al. . |
| 5,102,409 | 4/1992 | Balgorod . |
| 5,144,630 | 9/1992 | Lin . |
| 5,360,424 * | 11/1994 | Klopotek .................................. 606/4 |
| 5,620,436 * | 4/1997 | Lang et al. .............................. 606/4 |
| 5,980,513 * | 11/1999 | Frey et al. ............................ 606/10 |

FOREIGN PATENT DOCUMENTS

| | | |
|---|---|---|
| 0770370 * | 5/1997 | (EP) . |
| 8700748 | 2/1987 | (WO) . |
| WO 87/00748 | 2/1987 | (FR) . |
| 4111158 | 8/1991 | (WO) . |
| WO 91/11158 | 8/1991 | (WO) . |
| WO 95/27454 * | 10/1995 | (WO) . |

* cited by examiner

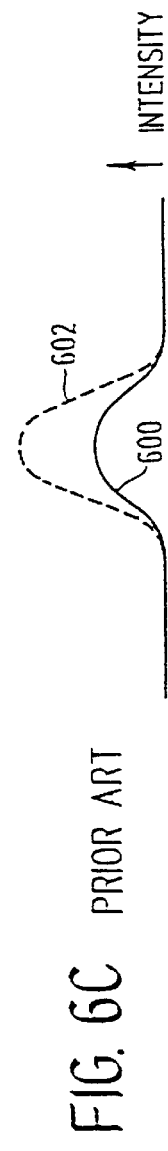
FIG. 6A PRIOR ART
FIG. 6B PRIOR ART
FIG. 6C PRIOR ART
FIG. 6D PRIOR ART
FIG. 6E PRIOR ART
FIG. 6F PRIOR ART
FIG. 6G PRIOR ART

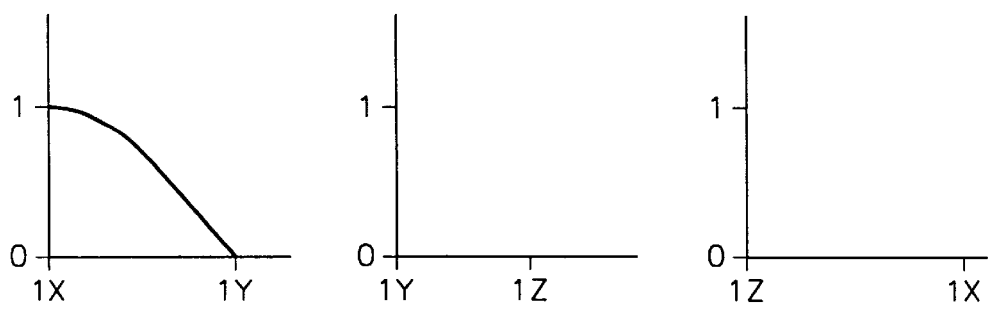
FIG. 7D1
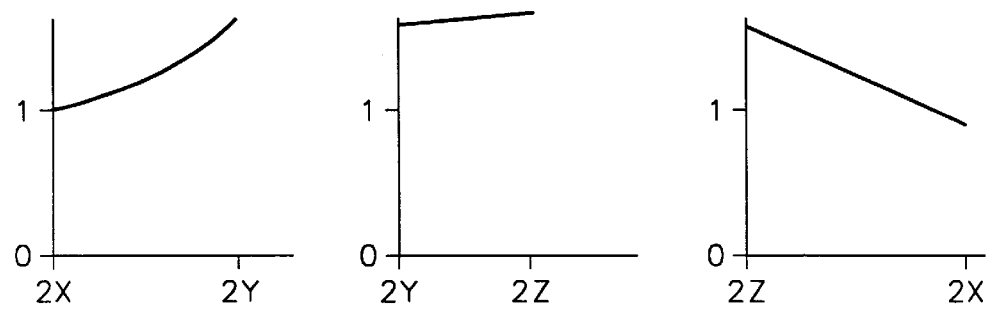
FIG. 7D2
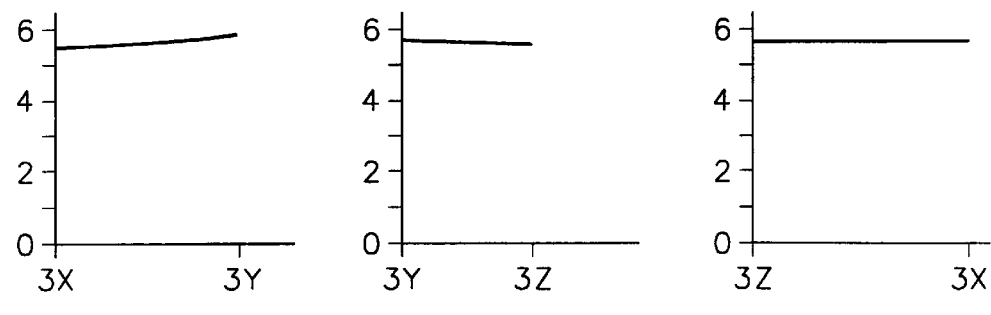
FIG. 7D3

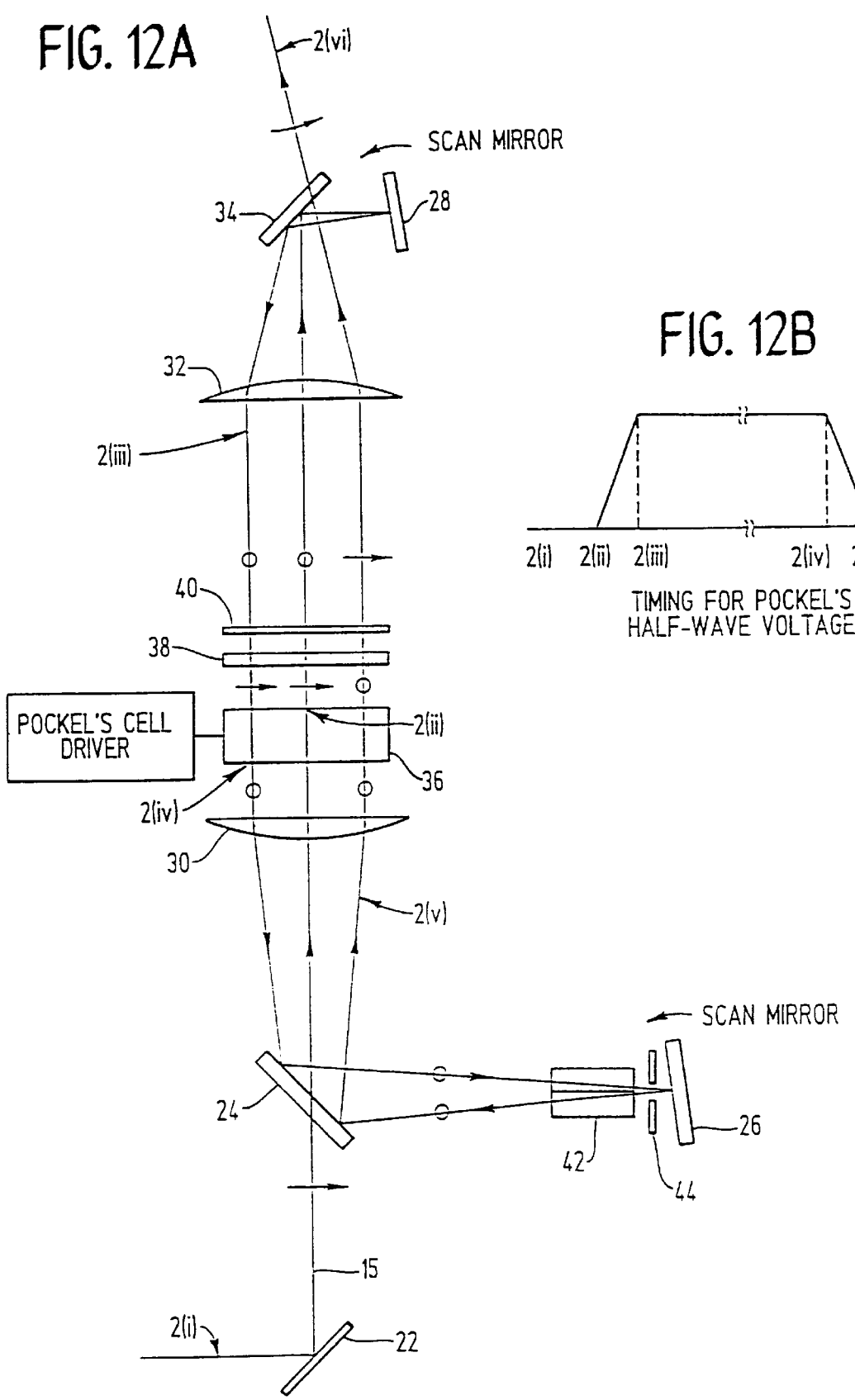

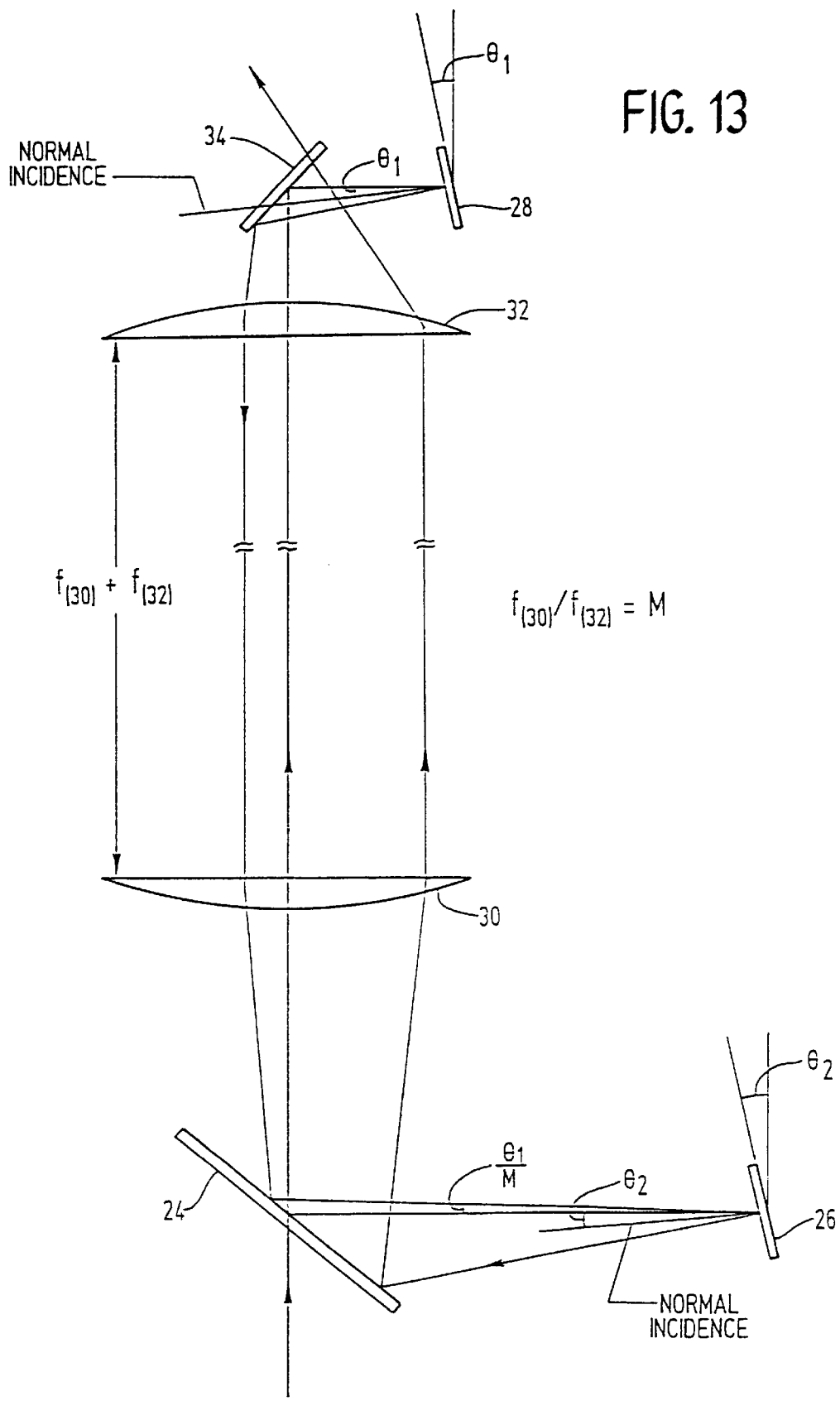

Ti : Al₂O₃ LASER ROD — 50

Al₂O₃ RING SLEEVE — 52

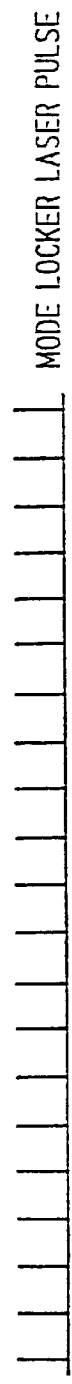
FIG. 17A  MODE LOCKER LASER PULSE
FIG. 17B  SYNCHRONIZATION PULSES FROM THE TIMER DIVIDER
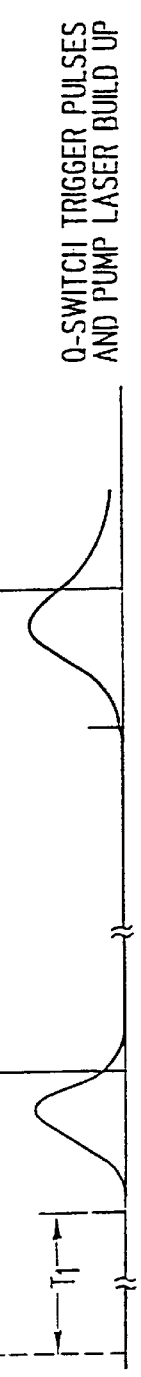
FIG. 17C  Q-SWITCH TRIGGER PULSES AND PUMP LASER BUILD UP
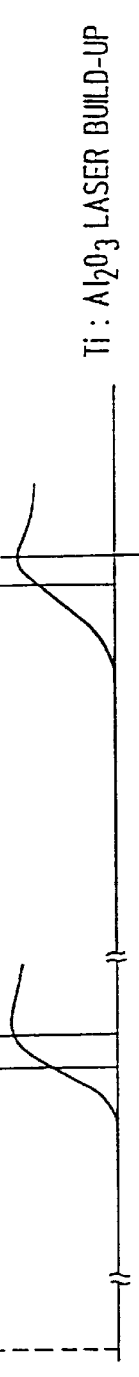
FIG. 17D  Ti:Al$_2$O$_3$ LASER BUILD-UP
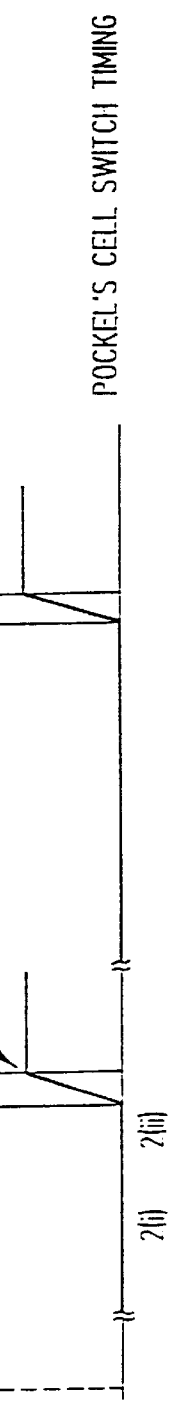
FIG. 17E  POCKEL'S CELL SWITCH TIMING

METHOD OF, AND APPARATUS FOR, SURGERY OF THE CORNEA

CROSS-REFERENCE TO RELATED APPLICATION

This application is a continuation of U.S. patent application Ser. No. 07/788,424 filed Nov. 6, 1991, now abandoned, and a continuation-in-part of U.S. patent application Ser. No. 07/740,004, filed Aug. 2, 1991, entitled "Two Dimensional Scanner-Amplifier Laser" now U.S. Pat. No. 5,280,491.

BACKGROUND OF THE INVENTION

1. Field of the Invention

This invention relates to methods of, and apparatus for, surgery of the cornea, and more particularly to a laser-based method and apparatus for corneal surgery.

2. Related Art

Art Related to the Inventive Method and Apparatus for Surgery

The concept of correcting refractive errors by changing the curvature of the eye was brought forth early on, as illustrated in the notable mechanical methods pioneered by J. Barraquer. These mechanical procedures involve removal of a thin layer of tissue from the cornea by a microkeratome, freezing the tissue at the temperature of liquid nitrogen, and re-shaping the tissue in a specially designed lathe. The thin layer of tissue is then re-attached to the eye by suture. The drawback of these methods is the lack of reproducibility and hence a poor predictability of surgical results.

With the advent of lasers, various methods for the correction of refractive errors have been attempted, making use of the coherent radiation properties of lasers, and the precision of the laser-tissue interaction. A $CO_2$ laser was one of the first to be applied in this field. Peyman, et al., in Ophthalmic Surgery, vol. 11, pp. 325–9, 1980, reported laser burns of various intensity, location, and pattern were produced on rabbit corneas. Recently, Horn, et al., in the Journal of Cataract Refractive Surgery, vol. 16, pp. 611–6, 1990, reported that a curvature change in rabbit corneas had been achieved with a $Co:MgF_2$ laser by applying specific treatment patterns and laser parameters. The ability to produce burns on the cornea by either a $CO_2$ laser or a $Co:MgF_2$ laser relies on the absorption in the tissue of the thermal energy emitted by the laser. Histologic studies of the tissue adjacent to burn sites caused by a $CO_2$ laser reveal extensive damage characterized by a denaturalized zone of 5–10 microns deep and disorganized tissue region extending over 50 microns deep. Such lasers are thus ill-suited to corneal laser surgery.

In U.S. Pat. No. 4,784,135, Blum et al. discloses the use of far-ultraviolet radiation of wavelengths less than 200 nm to selectively remove biological materials. The removal process is claimed to be by photoetching without requiring heat as the etching mechanism. Medical and dental applications for the removal of damaged or unhealthy tissue from bone, removal of skin lesions, and the treatment of decayed teeth are cited. No specific use for cornea surgery is suggested, and the indicated etch depth of 150 microns is too great for most corneal surgery purposes. Further, even though it is suggested in this reference that the minimum energy threshold for ablation of tissue is 10 $mJ/cm^2$, clinical studies have indicated that the minimum ablation threshold for excimer lasers at 193 nm for cornea tissue is about 50 $mJ/cm^2$.

In U.S. Pat. No. 4,718,418, L'Esperance, Jr. discloses the use of a scanning laser characterized by ultraviolet radiation to achieve controlled ablative photodecomposition of one or more selected regions of a cornea. According to the disclosure, the laser beam from an excimer laser is reduced in its cross-sectional area, through a combination of optical elements, to a 0.5 mm by 0.5 mm rounded-square beam spot that is scanned over a target by deflectable mirrors. (L'Esperance has further disclosed in European Patent Application No. 151869 that the means of controlling the beam location are through a device with a magnetic field to diffract the light beam. It is not clear however, how the wave front of the surgical beam can be affected by an applied magnetic to any practical extent as to achieve beam scanning.) To ablate a corneal tissue surface with such an arrangement, each laser pulse would etch out a square patch of tissue. Each such square patch must be placed precisely right next to the next patch; otherwise, any slight displacement of any of the etched squares would result in grooves or pits in the tissue at the locations where the squares overlap and cause excessive erosion, and ridges or bumps of unetched tissue at the locations in the tissue where the squares where not contiguous. The resulting minimum surface roughness therefore will be about 2 times the etch depth per pulse. A larger etch depth of 14 microns per pulse is taught for the illustrated embodiment. This larger etch depth would be expected to result in an increase of the surface roughness.

Because of these limitations of laser corneal surgery systems, it is not surprising that current commercial manufactures of excimer laser surgical systems have adopted a different approach to corneal surgery. In U.S. Pat. No. 4,732,148, L'Esperance, Jr. discloses a method of ablating cornea tissue with an excimer laser beam by changing the size of the area on the cornea exposed by the beam using a series of masks inserted in the beam path. The emitted laser beam cross-sectional area remains unchanged and the beam is stationary. The irradiated flux and the exposure time determines the amount of tissue removed.

A problem with this approach is that surface roughness will result from any local imperfection in the intensity distribution across the entire laser beam cross-section.

Furthermore, the intended curvature correction of the cornea will deviate with the fluctuation of the laser beam energy from pulse to pulse throughout the entire surgical procedure. This approach is also limited to inducing symmetric changes in the curvature of the cornea, due to the radially symmetrical nature of the masks. For asymmetric refractive errors, such as those commonly resulting from cornea transplants, one set of specially designed masks would have to be made for each circumstance.

Variations of the above technique of cornea ablation have also been developed for excimer lasers. In U.S. Pat. No. 4,941,093, Marshall et al. discloses the use of a motorized iris in a laser beam path to control the beam exposure area on the cornea In U.S. Pat. No. 4,856,513, Muller discloses that re-profiling of a cornea surface can be achieved with an erodible mask, which provides a pre-defined profile of resistance to erosion by laser radiation. This method assumes a fixed etch rate for the tissue to be ablated and for the material of the erodible mask. However, etch characteristics vary significantly, depending on the type of the materials and the local laser energy density. The requirements of uniformity of laser intensity across the beam profile and pulse to pulse intensity stability, as well as limitation of the technique to correct symmetric errors, also apply to the erodible mask method.

Another technique for tissue ablation of the cornea is disclosed in U.S. Pat. No. 4,907,586 to Bille et al. By focusing a laser beam into a small volume of about 25–30 microns in diameter, the peak beam intensity at the laser focal point could reach about $10^{12}$ watts per $cm^2$. At such a peak power level, tissue molecules are "pulled" apart under the strong electric field of the laser light, which causes dielectric breakdown of the material. The conditions of dielectric breakdown and its applications in ophthalmic surgery had been described in the book "YAG Laser Ophthalmic Microsurgery" by Trokel. Transmissive wavelengths near 1.06 microns and the frequency-doubled laser wavelength near 530 nm are typically used for the described method. The typical laser medium for such system can be either YAG (yttrium aluminum garnet) or YLF (yttrium lithium fluoride). Bille et al. further discloses that the preferred method of removing tissue is to move the focused point of the surgical beam across the tissue. While this approach could be useful in making tracks of vaporized tissue, the method is not optimal for cornea surface ablation. Near the threshold of the dielectric breakdown, the laser beam energy absorption characteristics of the tissue changes from highly transparent to strongly absorbent. The reaction is very violent, and the effects are widely variable. The amount of tissue removed is a highly non-linear function of the incident beam power. Hence, the tissue removal rate is difficult to control. Additionally, accidental exposure of the endothelium by the laser beam is a constant concern. Most importantly, with the variation in the ablated cross-sectional area and the etch depth, sweeping the laser beam across the cornea surface will most likely result in groove and ridge formation rather than an optically smooth ablated area.

Other problems that occur with some of the prior art systems result from the use of toxic gases as the lasing material. This is particularly a problem with excimer lasers, which are frequently used in health clinic and hospital environments.

An important issue that is largely overlooked in all the above-cited references is the fact that the cornea is a living organism. Like most other organisms, corneal tissue reacts to trauma, whether it is inflicted by a knife or a laser beam. Clinical results have showed that a certain degree of haziness develops in most corneas after laser refractive surgery with the systems taught in the prior art. The principal cause of such haziness is believed to be surface roughness resulting from grooves and ridges formed while laser etching. Additionally, clinical studies have indicated that the extent of the haze also depends in part on the depth of the tissue damage, which is characterized by an outer denatured layer beneath which is a more extended region of disorganized tissue fibers. Another drawback due to a rough corneal surface is related to the healing process after the surgery: clinical studies have confirmed that the degree of haze developed in the cornea correlates with the roughness at the stromal surface.

For reliable ablation results, a current commercial excimer laser corneal surgery system operates at about 150–200 $mJ/cm^2$. The etch depth at 193 nm is about 0.5 microns per pulse, and the damage layer is about 0.3 microns deep. Light scattering from such a surface is expected.

It is therefore desirable to have a method and apparatus for performing corneal surgery that overcomes the limitations of the prior art. In particular, it is desirable to provide an improved method of cornea surgery which has accurate control of tissue removal, flexibility of ablating tissue at any desired location with predetermined mined ablation depth, an optically smooth finished surface after the surgery, and a gentler surgical beam for laser ablation action.

The present invention provides such a method and apparatus. The invention resolves the shortcomings of the current corneal surgical systems, including the use of toxic gases, limitations stemming from correcting only symmetric errors in the case of excimer laser systems, the extensive damage caused by $Co:MgF_2$ and $CO_2$ laser systems, and the uncertainty of the etch depth in the case of YAG or YLF laser systems.

Art Related to the Scanner-Amplifier Laser Invention

The control of laser beam positioning has become a key element in many fields of applications, such as image processing, graphic display, materials processing, and surgical applications involving precision tissue removal.

A general overview of the topic is given in "A Survey of Laser Beam Deflection Techniques", by Fowler and Schlafer, Proceedings of IEEE, vol. 54, no. 10, pages 1437–1444, 1966.

U.S. Pat. No. 3,432,771 to Hardy et al. issued Mar. 11, 1969, disclosed an apparatus for changing the direction of a light beam in an optical cavity. The cavity consists of a focussing objective located between two reflectors, such as curved mirrors. The relative position of one center of curvature with respect to the other center of curvature can be controlled by positioning of one of the mirrors. Points on the reflectors are located at the object and the image positions for the objective. When the active medium is suitably excited, the orientation of the lasing mode, and hence the position of the spots of light, is determined by the effective angular positions of the reflectors.

U.S. Pat. No. 3,480,875 to Pole, issued Nov. 25, 1969, disclosed a laser cavity which was set up between a pair of plane mirrors. At least one active laser element is located between the mirrors. A pair of lens systems are positioned between the mirrors so that they have a common focal plane between them. A Kerr cell, polarizers, and a compensator suppress light oscillation along certain reflector paths within the cavity, thereby setting up preferred modes of oscillation along other paths. Laser emission occurs along the preferred paths.

U.S. Pat. No. 3,597,695 to James E. Swain, issued Aug. 3, 1971, disclosed an apparatus for amplifying laser light by multiple passes through a lasing material in a single laser cavity. A single amplifier stage achieved what had been accomplished by several stages. This is accomplished by a switching mechanism which directs a laser beam into and out of the cavity at selected time intervals, thereby enabling amplification of low intensity laser pulses to an energy level near the damage limits of the optical components of the system.

U.S. Pat. No. 4,191,928 to John L Emmett, issued Mar. 4, 1980, disclosed a high energy laser system using a regenerative amplifier which relaxes all constraints on laser components other than the intrinsic damage level of matter, so as to enable use of available laser system components. This can be accomplished by use of a segmented component spatial filter.

Many techniques have been developed for controlling the laser beam direction. For the purpose of this invention, this discussion will be limited to the speed, accuracy, and the scan angle range of different devices used in a random access mode.

Galvanometer mirror scanners have a large scan angle range. However, the mechanical response due to the balance of the coil and the applied magnetic field is limited to a few hundred hertz. The settling time and oscillation about the equilibrium point further limits the accuracy attainable with such devices.

Mirrors positionable with piezo actuators are capable of an accurate hunt-free movement response of up to tens of kilohertz, depending on the design of the mounts. The typical scan angle is on the order of a few milli-radians. Methods to enhance the scan angle have been proposed by J. Schlafer and V. J. Fowler, "A Precision, High Speed, Optical Beam Scanner", Proceedings, International Electron Devices Meeting, 1965. In their report, multiple scanning piezo-mirrors where used to intercept a laser beam, such that the scan angle of each scanner contributes to the total effect, which is the sum of all scan angles. This device requires many individual scanner units, which multiplies in economic cost with the number of units. The mirror size also limits the number of units that can be used before the beam will miss the last mirror.

Furthermore, both of the above methods are applicable in one dimensional scanning only. For two-dimensional scans, an additional unit, which is either an identical or a mix with another device, must be provided for scanning in the other dimension, doubling cost and space requirements.

In U.S. Pat. No. 3,480,875 to R. V. Pole, disclosed is a scanning laser device, in which the spatial orientation of the laser beam in the resonant cavity is controlled by passing through a combination of a retardation plate and a Kerr cell inside the laser cavity. At a specific angle, as determined by the Kerr cell, loss is minimum for the laser beam, and therefore the laser beam will oscillate in that preferred direction. While this method allows scanning of large angles, the scan speed is limited by the laser build-up time, for which the laser beam intensity will be re-established at each new beam direction. Another drawback of this arrangement is the variation in the laser intensity during the laser build-up.

In U.S. Pat. No. 3,432,771 to W. A. Hardy, disclosed is another scanning laser, in which the optical cavity consists of a focussing objective, and spherical reflectors, or equivalent optics which consist of a lens and a plane mirror. The scan angle is magnified most effectively in an optical arrangement in which the two end reflectors form a nearly concentric cavity with the focussing lens at the center of focus. The drawback is that the cavity tolerates diverging beams to build up inside the cavity, as illustrated in FIG. 1 of the patent, hence the laser output has a high content of multiple transverse modes. By increasing the radius of curvature of the scan mirror and keeping its location fixed, the multi-mode content can be reduced, but the scan range will approach that of the actual scan angle with a possible small magnification factor. As suggested by its preferred embodiment with an electro-optical beam deflector, the scan angle will be only a few milli-radians if a near diffraction-limited laser beam is to be produced.

It would thus be desirable to have a scanner-amplifier unit which accepts a low energy laser pulse and emits an amplified laser pulse at a predetermined angular positions in two dimensions. The present invention provides such a unit.

SUMMARY OF THE INVENTION

The optimal surgical method for the cornea can be best appreciated from the characteristics required of the cornea to perform its important functions. The corneal surface is the first optical interface where all light enters into the eye and thereafter forms images at the retina. Corneal shape, degree of smoothness, and clarity all determine visual acuity and the contrast sensitivity of the vision system. Hence, the importance of the optical quality of the cornea cannot be over-emphasized.

The physical limits on the allowable surface roughness of the cornea can be understood by noting the following facts: human photo-sensors on the retina have a wavelength sensitivity range of about 380–850 nm in the optical spectrum; surface roughness exceeding half of the wavelength within the sensitivity range will act as light scattering centers; therefore, any inhomogeneity of the cornea surface or the inside stromal layer ideally should be kept at or below 0.2 microns to achieve an optically-smooth cornea surface.

The present invention recognizes that an optically smooth corneal surface and a clear cornea (including post-operative clarity) are all critical to successful refractive corneal surgery. The invention was developed with a particular view to preserving these characteristics.

The preferred method of performing a surface ablation of cornea tissue or other organic materials uses a laser source which has the characteristics of providing a shallow ablation depth (0.2 microns or less per laser pulse, and preferably 0.05 microns or less per laser pulse), and a low ablation energy density threshold (less than or equal to about 10 $mJ/cm^2$), to achieve optically smooth ablated corneal surfaces. The preferred laser system includes a Ti-doped $Al_2O_3$ laser emitting from about 100 up to about 50,000 laser pulses per second, and preferably about 10,000 laser pulses per second. The laser wavelength range is about 198–300 nm, with a preferred wavelength range of about 198–215 nm, and a pulse duration of about 1–5,000 picoseconds. The laser beam cross-sectional area varies from 1 mm in diameter to any tolerably achievable smaller dimension, as required by the particular type of surgery.

According to the present invention, each laser pulse is directed to its intended location on the surface to be ablated through a laser beam control means, such as the type described in a co-pending, commonly-owned patent application for an invention entitled "Two Dimensional Scanner-Amplifier Laser" (U.S. patent application Ser. No. 07/740, 004). The present invention also discloses a method of distributing laser pulses and the energy deposited on a target surface such that surface roughness is controlled within a specific range.

Additionally, the preferred apparatus for performing corneal surgery includes a laser beam intensity monitor and a beam intensity adjustment means, such that constant energy level is maintained throughout the operation. The location for the deposition of each pulse of laser energy relative to the surface to be ablated is controlled by monitor means such that eye movement during the operation is corrected for by a corresponding compensation in the location of the surgical beam. Provision for a safe and efficacious operation is included in the preferred apparatus, such that the operation will be terminated if the laser parameters or the eye positioning is outside of a predetermined tolerable range.

According to the present invention, various surgical procedures can be performed to correct refractive errors or to treat eye diseases. The surgical beam can be directed to remove cornea tissue in a predetermined amount and at a predetermined location such that the cumulative effect is to remove defective or non-defective tissue, or to change the curvature of the cornea to achieve improved visual acuity. Incisions on the cornea can be make in any predetermined length and depth, and they can be in straight line or curved patterns. Alternatively, circumcisions of tissue can be made to remove an extended area, as in a cornea transplant.

Although the primary use of the present invention is in ophthalmology, the laser ablation process can be applied in areas of neurology for microsurgery of nerve fibers, cardiology for the removal of plaque, and urology for the removal of kidney stones, just to mention a few possible uses. The present invention can also be useful for applications in micro-electronics in the areas of circuit repair, mask fabrication and repair, and direct writing of circuits.

The present invention provides an improved method of cornea surgery which has accurate control of tissue removal, flexibility of ablating tissue at any desired location with predetermined ablation depth, an optically smooth finished surface after the surgery, and a gentle surgical beam for laser ablation action.

The present invention also discloses a new method of reshaping a cornea surface with an optically smooth finish by depositing the laser energy in a prescribed pattern at predetermined locations. This is accomplished with high speed, precision control of the beam location, as disclosed in co-pending U.S. application Ser. No. 07/740,004 for an invention entitled "A Two Dimensional Scan-Amplifier Laser."

The present invention also discloses a means to improve accuracy and reproducibility of eye surgery by adjusting the surgical beam direction to compensate for any eye movement during the surgical procedure. In addition, the surgical beam intensity, beam intensity profile, diameter, and location are monitored and maintained during the surgery.

Objects with Respect to the Inventive Method and Apparatus for Surgery

In accordance with the above discussion, these and other functions can be accomplished according to the teachings of the present invention, which provides a new and improved laser source, providing a gentler surgical beam and a shallower tissue etch depth than taught in the prior art It is another object of the present invention to provide an improved apparatus and method for removing organic materials from the surface of living or non-living objects. The present invention is specifically useful for the ablation of tissue on the cornea.

It is another object of the present invention to provide a method of ablating cornea or other organic materials to achieve an optically smooth surface.

It is another object of the present invention to provide new means of laser cornea surgery, with a new laser source emitting a large number of laser pulses (about 100 to 50,000 laser emissions per second), each of which etches a shallow depth (about 0.2 microns or less) of the cornea tissue.

It is another object of the present invention to provide new means of laser cornea surgery, with a new laser source emitting a wavelength of about 198–300 nm, with a preferred range of about 198–215 nm, and a pulse duration of about 1–5,000 picoseconds.

It is another object of the present invention to provide means of depositing surgical laser beam energy with a beam control as described in co-pending U.S. application Ser. No. 07/740,004, for an invention entitled "A Two Dimensional Scan-Amplifier Laser," to achieve exact positioning of each laser pulse.

It is another object of the present invention to provide a gentler ablative surgery, with significantly reduced damage and trauma of the tissue or organic materials adjacent to the ablation site, in comparison to the prior art.

It is another object of the present invention to provide means to remove cornea tissue or other organic materials at predetermined locations, over predetermined areas, and with predetermined depths of ablation.

It is a specific object of the present invention to correct refractive errors, including myopia, hyperopia, and astigmatism, of the eye. It is another specific object of the present invention to correct refractive errors that may be spherically symmetric or asymmetric.

It is another object of the present invention to remove scars, tumors, and infected or opaque tissue on the cornea.

It is another object of the present invention to provide an improved method for performing a cornea transplant operation.

It is another object of the present invention to provide an improved method of making incisions on the cornea, to achieve correction of myopia and/or astigmatism.

It is another specific object of the present invention that the inventive methods be automated with computer control for accurate and safe operation.

It is yet another specific object of the present invention to provide control means for compensating for eye movement during an operation by making a corresponding adjustment of the surgical beam location.

Objects with Respect to the Scanner-Amplifier Laser Invention

The following objects are in accordance with the teachings of the co-pending, commonly-owned patent application for the invention entitled "Two Dimensional Scanner-Amplifier Laser" (U.S. patent application Ser. No. 07/740, 004).

An object in accordance with the present invention is to provide a scanner-amplifier unit which accepts a low energy laser pulse and emits an amplified laser pulse at a predetermined angular positions in two dimensions.

It is another object of this invention to disclose a construction of a high speed scanner-laser amplifier system, which has the capability of large scan angles, and the capability of emitting high quality, near diffraction limited laser beam. The scanner of the present invention can position a laser beam in two dimensions in a random access mode at high speed.

It is another object of the invention that the scanner-amplifier system generate ultra-short laser pulses of 1–500 picoseconds duration at a multi-kilohertz repetition rate, and that the energy of each laser pulses is amplified in a controlled manner to a desired level up to the damage level of the optical components.

It is another object of the invention that the laser medium is to be pumped by a plurality of laser beams in a longitudinal direction, such that high excitation density is achieved in the laser medium.

It is another object of the invention that the scanner-amplifier system can place an individual high energy laser pulse at a precisely intended angular location in a two-dimensional space.

It is yet another object of this invention to construct a Ti:$Al_2O_3$ laser with a high laser pulse rate, in the range of 1000 to 50,000 pulses per second, and with high average laser power, in the range of several watts or higher.

It is an object of this invention that each laser pulse has high peak power, and a short pulse duration, of sub-picoseconds to hundreds of picoseconds.

Still another object of this invention is to generate stable and high conversion efficiency in the second harmonic laser wavelength, which is used to generate population inversion in the Ti:$Al_2O_3$ laser medium.

It is an object of this invention to provide a novel method to attain high pump power in the second harmonic wavelength for the Ti:$Al_2O_3$ laser.

It is an object of this invention to propose a novel method to attain high pump power in an end-pumping configuration for the Ti:$Al_2O_3$ laser.

The preferred method for controlling the direction of the laser beam consists of a pair of scanning mirrors driven by piezo actuators. The mirror pair are driven in tandem. The scan angles of the mirror pair are summed and amplified by an optical arrangement. Two convergent spherical lenses of un-equal focal length are arranged between the scanning mirrors in such a way that a laser beam will be travelling inside the cavity in which the boundary is defined by the scan mirrors. For each round trip of the laser beam inside the cavity, the angle of the laser beam to an exit window increases as a multiple of the actual scan angles of the scan mirrors.

In accordance with this invention, the direction of the laser beam emitted from the scanner-amplifier system is controllable in two dimensions, at high speed, and with high precision.

In a preferred embodiment, the laser beam is generated by an amplifying means with a seeding laser pulses. Optical retardation plate, Pockels cell, and polarization dependent optical elements are used for the control of a seed laser beam and for directing that laser beam in the amplifier cavity. A laser gain medium is included in the cavity. Means for exciting the laser medium, and for generating multi-kilohertz, ultra-short duration laser pulses, are disclosed in the invention. Means for controlling the timing and the synchronization of the seed pulse, the pump source, and the amplified laser pulses inside the scanner-amplifier cavity are also provided.

It is an object of this embodiment to provide a means and method for combining a plurality of laser beams to provide a high power laser beam source.

It is another object of the invention to provide a combiner for combining a plurality of laser beams that does not require any form of specific polarization in any of the component beams. It is an object of such a combiner that it can form a beam bundle consisting of large number of beams in a small cross section.

It is yet another object of this invention to provide a novel method of combining a plurality of laser beams to provide a high power laser beam source for an end-pumping configuration of a laser beam. The combiner eliminates limitations imposed by the physical size of the beam steering optics and the optical mounts (an earlier method of beam combining relies on the direction of the linear polarization, and this method is limited to combining two beams only).

The details of the preferred embodiments of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 6A is a diagram of a first laser beam intensity profile in accordance with the prior art.

FIG. 6B is a diagram of a corneal etch profile resulting from the laser beam intensity profile shown in FIG. 6A.

FIG. 6C is a diagram of second and third laser beam intensity profiles in accordance with the prior art.

FIG. 6D is a diagram of the corneal etch profiles resulting from the laser beam intensity profiles shown in FIG. 6C.

FIG. 6E is a diagram of a pattern of laser beam intensity profiles in accordance with the prior art.

FIG. 6F is a diagram of the laser beam intensity profile resulting from the pattern shown in FIG. 6E.

FIG. 6G is a diagram of a corneal etch profile resulting from the laser beam intensity profile shown in FIG. 6F.

FIGS. 7D1–7D3 are sets of graphs showing the crest-to-trough distances of level one, level two, and level three etch patterns in accordance with the present invention.

FIG. 12A is a schematic diagram showing a second embodiment of the integrated scanner-amplifier unit of the invention.

FIG. 12B shows a voltage signal applied to the Pockel's cell.

FIG. 13 is a schematic diagram showing the process of angular amplification for the laser beam inside the scanner-amplifier cavity.

FIGS. 17A–17E are diagram showing the synchronization between the mode-locked laser pulses, the selected laser pulses after the timer-divider circuit, the Q-switched laser pulses for pumping the gain medium, and the half-wave optical switch wave form.

Like reference numbers and designations in the various drawings refer to like elements.

DETAILED DESCRIPTION OF THE INVENTION

Figure 1:
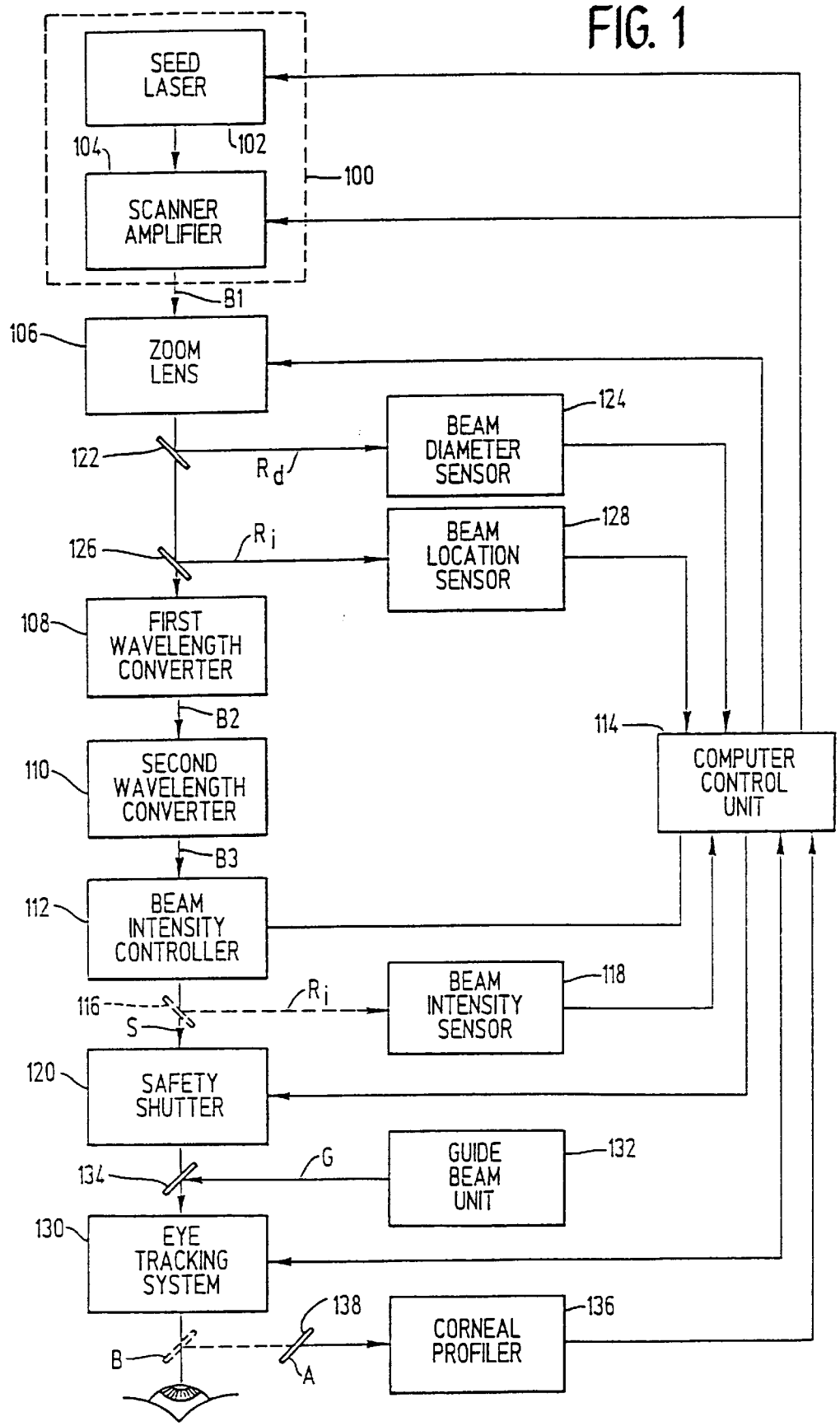
FIG. 1 is a block diagram of the preferred embodiment of the inventive apparatus.

Throughout this description, the preferred embodiment and examples shown should be considered as exemplars, rather than limitations on the method and apparatus of the present invention.

Background Information

The laser apparatus and system disclosed in this invention is for achieving two principal objectives:

(1) The damage zone underneath the material ablated by the present laser system must be substantially reduced in comparison to prior art laser systems.

(2) For each laser pulse deposited on the cornea, a definite predetermined depth of tissue is to be ablated. The ablated depth per laser pulse must be controllable and about 0.2 microns or less, and preferably about 0.05 microns or less.

A brief discussion on the mechanism of the ablation process is useful to understand how the stated objectives can be achieved by the teaching of the present invention. It is a well-known fact that laser ablation can occur when the laser beam intensity is increased beyond a certain level. The actual ablation conditions however, vary depending on the characteristics of a wide range of laser parameters and the composition of the material to be ablated. For the purposes of the present invention, only those aspects that are relevant to the two principal objectives will be discussed.

When laser energy is absorbed in an organic material, on the most basic level, the electronic configuration of the target polymer molecules makes a transition to one of its excited electronic states. Each polymer is made of hundreds or more of sub-units of smaller molecules called monomers. The monomers are made of even smaller units of radicals consisting of combinations of hydrogen, carbon, oxygen, and nitrogen atoms. Depending on the energy level of the laser photons, a polymer can be broken into constituent monomers, radicals, or ionized atoms. For a laser having a wavelength near 200 nm, a single laser photon is not sufficiently energetic to break any molecular bond. However, after absorbing an initial photon, a molecule is promoted to an excited electronic state configuration, with its electrons in higher energy orbits.

With increased power levels of the laser beam, the excited electron density increases correspondingly. At the same time, the excited electrons migrate down the polymeric chain of the organic material, and spread towards the bulk volume with lower excited state density. The present invention recognizes that the excited state electronic orbitals are the means for energy storage that will eventually fuel the ablation process, and the electronic energy state migration process plays a key role in the dynamics controlling the initiation of the laser ablation.

As the laser beam intensity increases further towards the ablation threshold, the excited electron density reaches a critical volume density such that the electronic orbitals can pair and transfer the sum of their energy to a single electron orbital. This process breaks the molecule into two or more pieces, and releases an energetic electron. At this point, the organic medium is damaged but not yet ablated.

Consider now the geometric distribution of the excited state orbitals in an organic material. As the laser light is absorbed in the organic material, by Beer's law, the front surface where the material is first exposed encounters most of the laser photons, and the beam intensity decreases exponentially as it traverses deeper into the material. Hence, the spatial distribution of the excited state density also decreases accordingly, characteristic of the absorption coefficient of the material at the laser wavelength. It follows that the slope of the distribution curve of the excited state density is directly related to the absorption coefficient. Additionally, the steeper the slope of the excited state density distribution curve, the more spatially localized is the excited state density. The preferred range of the absorption depth of the surgical laser beam in the cornea is less then about 50 microns.

Alternatively, the ablation threshold can be reached at a lower laser peak power, provided that the material is exposed for a longer period. In accordance with the discussion above, if the total integrated energy of a laser pulse is the same as that of a shorter pulse, the excited state density established by the longer pulse would be lower due to the additional time available for energy migration out of the irradiated volume. Therefore, to achieve the same ablation threshold for a longer pulse, the longer pulse must have a larger total integrated energy than a shorter pulse having the same ablation threshold. Empirical results obtained from materials damage indicate that a particular damage threshold can be reached with a pulsed laser beam 100 times longer in duration than a shorter duration pulse, provided that the total integrated energy of the longer laser pulse is increased by about 10 fold over the integrated energy of the shorter pulse.

In accordance with the discussion above, when using longer duration pulses, the energy migration process is counter-balanced by additional laser beam pumping to build up the critical excited state density. Importantly, with a longer laser pulse, the excited state orbitals diffuse from the front surface into the depth of the material (along the laser beam direction). Hence, the excited state distribution curve will have less steep a slope compared to the curve from a shorter pulse. The present invention recognizes that the depth of the corneal layer which has sufficient excited state orbitals to satisfy the damage threshold condition will be correspondingly deepened. Therefore, the corneal damage inflicted by a longer duration laser pulse is more extensive than the damage inflicted with a shorter duration pulse.

In consideration of these observations and characteristics, the present invention uses short duration laser pulses of about 1–5,000 picoseconds to reduce inflicted damage to target tissues.

The other key objective of the present invention is to achieve a shallow yet reproducible etch depth at the cornea surface from each laser pulse. It is important to note that a reproducible etch depth will not necessarily be attained at reduced levels of laser energy per pulse, especially when the energy level is close to being at an arbitrarily small value above the ablation energy threshold. For an excimer laser, the typical laser energy density in the surgical beam required for cornea ablation is about 150–250 mJ/cm². The ablation threshold level for excimer laser is at about 50 mJ/cm²; basically no ablative action can be observed at a laser energy density below this threshold level.

It is also important to note that observation of ablative action near the threshold condition is determined by a statistical process. That is, determination of the average etch depth for laser beam energies near the ablation energy threshold are derived by measuring actual etch depth after hundreds or sometimes thousands of laser pulses over the same location, and determining an average etch depth per pulse. On a single shot basis, however, the etch depth could vary significantly, and most of the laser pulses may not ablate any material at all.

Therefore, to ensure a reliable etch depth for each single laser pulse, the present invention recognizes that the operating energy per pulse has to be set at a multiple of the ablation energy threshold level; a factor of 3 to 4 times the ablation energy threshold is usually sufficient to achieve satisfactory results. Accordingly, the present invention uses an ablation energy density of less than or equal to about 10 mJ/cm² to achieve a reproducible single-pulse etch rate of about 0.2 microns or less per laser pulse, and preferably 0.05 microns or less per laser pulse. This contrasts with current excimer lasers, which only provide reproducible single-pulse etching at an etch rate of no less than about 0.3–0.5 microns per laser pulse, with consequent light scattering due to cornea surface irregularities.

The present invention also recognizes the benefits of ablating cornea with a laser beam having a low energy density. A gentle laser beam, one that is capable of operating at a lower energy density for the surgical procedures, will clearly have the advantage of inflicting less trauma to the underlying tissue. The importance of this point can be illustrated by considering the dynamics of the ablation process on a microscopic scale: the ablation process is basically an explosive event. During ablation, organic materials are broken into their smaller sub-units, which cumulate a large amount of kinetic energy and are ejected out of the host surface at a supersonic velocity. The tissue beneath the ablated region absorbs the recoil forces from such elections. The present invention recognizes that a shallower etch depth involves less ejected mass per area, and hence reduces the recoil forces correspondingly. In accordance with the foregoing discussion, the laser characteristics of the present surgical system provide for an energy density that results in a reproducible single-pulse etch rate of only about 0.2 microns or less per pulse, and preferably about 0.05 microns or less per pulse. Such a shallow etch rate means less mass ejected per laser pulse. The damage impact on the underlying tissue is less by about a factor of 10 in comparison with the lowest etch rate attainable in the prior art.

Another way to reduce the shock to the cornea is by using a smaller beam area at the cornea to reduce the integrated recoil forces. Consequently, the laser beam cross-sectional area of the invention varies from 1 mm in diameter to any tolerably achievable smaller dimension, as required by the particular type of surgery. This characteristic of the invention contrasts with current excimer laser surgical systems, which subject an ablation zone to a surgical beam that is 4–6 mm in diameter.

In summary, the preferred laser corneal surgical system ablates corneal tissue a reproducibly at a single-pulse etch rate of about 0.2 microns or less per laser pulse, and preferably about 0.05 microns or less per laser pulse. In accordance with the present invention, a laser source with a wavelength range of about 198–300 nm (with a preferred range of about 198–215 nm), and a pulse duration of about 1–5,000 picoseconds, achieves reliable single pulse ablation on the cornea. The intensity of the laser pulses is regulated to have an ablation energy density of less than or equal to about 10 mJ/cm².

The Inventive Apparatus

FIG. 1 shows the preferred configuration of the inventive apparatus. A laser unit 100 generates an initial laser beam B1. The laser unit 100 is of the type that can output a beam rapidly deflectable or scannable under electronic control in two dimensions to any location in an area defined by orthogonal X and Y axes. One such laser unit is described in detail in the co-pending, commonly-owned patent application for invention entitled "Two Dimensional Scanner-Amplifier Laser" (U.S. patent application Ser. No. 07/740,004), and in the pertinent text reproduced below.

The initial laser beam B1 comprises a sequence of laser pulses having a pulse repetition rate of about 100 to 50,000 pulses per second. Each laser pulse has a pulse duration which can be varied from 1 picosecond to about 5,000 picoseconds. The actual number of laser pulses used for a surgery is determined by the amount of tissue to be removed.

In a preferred embodiment, the laser unit 100 includes a seed laser 102 and a scanner-amplifier laser 104. Preferably, the laser media in both the seed laser 102 and the scanner-amplifier 104 is a Ti-doped $Al_2O_3$ solid state laser crystal. Further details of the structure and operation of the laser unit 100 are set forth below.

After emerging from the laser unit 100, the laser beam B1 passes through a computer-controllable, motorized zoom lens 106, which provides control over the diameter of the laser beam B1. In practice, the zoom lens 106 may be placed in a number of suitable positions along the optical path of the laser beam between the laser unit 100 and a target. The motor actuation of the zoom lens 106 may be by any known means, such as electrical gear drives or piezoelectric actuators.

The preferred laser wavelength for the initial laser beam B1 is in the range of about 790–860 nm. The laser photon energy in the initial laser beam B1 is then converted in a first wavelength converter 108 (described below) by nonlinear wave mixing to a second laser beam B2 having approximately twice the initial laser beam photon energy, and a wavelength in the range of about 395–430 nm.

To attain the preferred operating laser wavelengths of about 198–215 nm, the second laser beam B2 is passed through a second wavelength converter 110 (described below). The laser photon energy in the second laser beam B2 is again converted by nonlinear wave mixing to a third laser beam B3 having approximately four times the initial laser beam photon energy, and a wavelength in the range of about 198–215 nm.

In an alternative embodiment, the initial laser beam B1 may be wavelength converted to the desired wavelength range of about 198–215 nm using a one-step converter (described below).

Surgical Laser Beam Control System

While the third laser beam B3 could be used directly for surgical purposes, in the preferred embodiment, the entire surgical laser apparatus includes a number of control and safety systems. In particular, the present invention includes means for monitoring and controlling the intensity of the beam, means for blocking the surgical beam in the event of a malfunction, means for monitoring and controlling the laser beam diameter and intensity profile, and means for verifying the two-dimensional (X-Y) scan position of the surgical beam.

Referring again to FIG. 1, the third laser beam B3 passes through a beam intensity controller 112, the output of which is the surgical laser beam S. The beam intensity controller 112 permits regulation of the energy of each laser pulse so that the etch depth of each pulse may be precisely controlled.

In the preferred embodiment, the beam intensity controller 112 is an electro-optical filter, such as an electrically activated Pockels cell in combination with an adjacent polarizing filter. The Pockels cell may include, for example, $LiNbO_3$, or any other electro-optical crystal, such as potassium dihydrogen phosphate ($KH_2PO_4$), also known as KDP. Pockels cells are commercially available from several sources, including Medox Electro-Optics of Ann Arbor, Mich. With the application of electric voltage across the electro-optical crystal in a Pockels cell, up to a half-wave retardation in the electric field vector of the incident laser beam can be generated. Depending on applied electrical voltage, the linear polarization of a laser beam traversing the crystal can be retarded from a horizontal polarization to vertical, or vice versa. The polarizer placed adjacent the Pockels cell acts as a selector with respect to the incident beam from the Pockels cell. As is known, if the beam impinging on the polarizer is orthogonally polarized by the Pockels cell, the beam will be essentially blocked by the polarizer. Lesser degrees of retardation generated by the Pockels cell will result in some of the light passing through the polarizer. By controlling the amount of retardation generated in the Pockels cell, the intensity of the incident laser beam can be electrically controlled.

In the preferred embodiment, the beam intensity controller 112 is coupled to a computer control unit 114, which is suitably programmed to vary the intensity of the output surgical laser beam S as required for a particular surgical procedure. The degree of retardation as a function of applied electrical signal can be ascertained by standard calibration techniques. The preferred location of the beam intensity control unit 112 is as shown in FIG. 1. However, the beam intensity control unit 112 can be placed at several suitable locations in the beam path between the laser unit 100 and a target. In the preferred embodiment, the intensity of the surgical beam S is regulated to have an ablation energy density of less than or equal to about 10 $mJ/cm^2$.

The present invention optionally provides for positive feed-back measurement of the beam intensity. A partially transmissive beam-splitting mirror 116 is placed after the beam intensity controller 112, and the reflected beam $R_i$ is directed to a beam intensity sensor 118. The beam intensity sensor 118 may be simply a photocell, although other elements, such as focussing optics, may be included. By monitoring the electrical output of the beam intensity sensor 118 with the computer control unit 114, the intensity of the surgical laser beam S can be positively measured to verify the proper operation of the beam intensity controller 112. The output of the beam intensity sensor 118 as a function of intensity of the surgical laser beam S can be ascertained by standard calibration techniques.

The inventive system also preferably includes a safety shutter 120, which is coupled to the computer control unit 114. The safety shutter 120 may be, for example, a mechanically-actuated shutter operated in a "fail-safe" mode. For example, the safety shutter 120 may include a solenoid-actuated shield that is positively held open by application of electrical energy to the solenoid. Upon command of the computer control unit 114, or failure of the entire system, electrical energy to the solenoid is cut off, causing the solenoid to retract the shield into position to block the path of the surgical laser beam S.

Alternatively, the safety shutter 120 may include a Pockels cell and polarizer configured as a light valve, with the Pockels cell biased with respect to the polarizer by application of an electrical voltage such that maximum light is normally transmitted by the combination. Cessation of the applied voltage will cause the output of the Pockels cell to become polarized orthogonal to the transmission direction of the polarizer, hence blocking the surgical laser beam S. Using this alternative configuration, the safety shutter 120 and the beam intensity controller 112 may be combined into a single unit.

Any other suitable means for quickly blocking the surgical laser beam S on command or in the event of system failure may be used to implement the safety shutter 120. In practice, the safety shutter 120 may be placed in a number of suitable positions along the optical path of the laser beam between the laser unit 100 and a target.

To control beam diameter, the inventive system provides a partially transmissive beam-splitting mirror 122 that reflects part of the beam $R_d$ to a beam diameter sensor 124. In practice, the beam diameter sensor 124 may be placed in a number of suitable positions along the optical path of the laser beam between the laser unit 100 and a target.

Figure 2A:
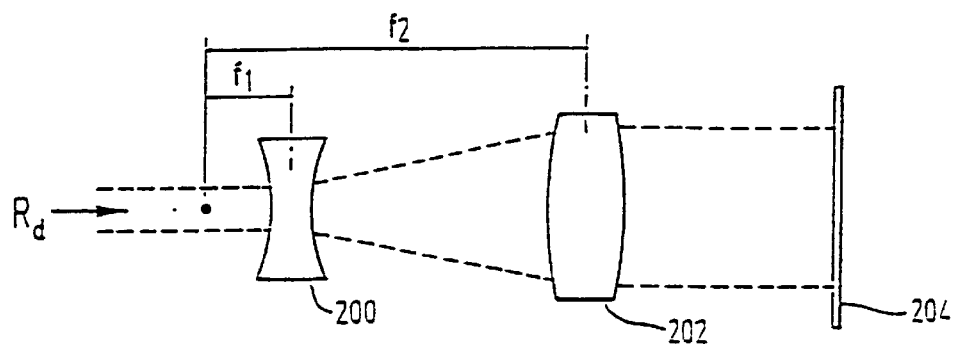
FIG. 2A is a side view of a beam diameter sensor, including an imaging device, in accordance with the present invention.

Referring to FIG. 2A, the beam diameter sensor 124 preferably includes at least a diverging (concave) lens 200 and a converging (convex) lens 202 configured as a magnifying telescope (i.e., the two lenses have a common focal point, with the focal length $f_2$ of the converging lens 202 being greater than the focal length $f_1$ of the diverging lens 200, and having optical centers aligned with the incident laser beam in its un-deflected position). The incident beam $R_d$ enters the diverging lens 200 and exits the converging lens 202. Such a configuration of lenses, while enlarging the incident beam, will also reduce the scan angle of the exiting beam.

Figure 2B:
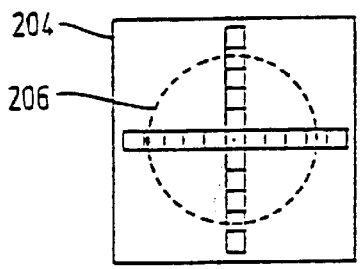
FIG. 2B is a front view of the imaging device of FIG. 2A.

The resulting enlarged beam is directed to a low density, low contrast imaging device 204, such as a charge-coupled device (CCD) camera. In the preferred embodiment, a CCD camera having a 64×64 pixel array with two or more bits of contrast is suitable. Such cameras are available commercially. The two lens 200, 202 are chosen to expand the incident beam $R_d$ so that the largest possible diameter 206 for the beam just fits within the imaging device 204 (see FIG. 2B, which shows only one row and one column of pixels).

In the preferred embodiment, the size of the beam is determined by periodically addressing a central row and a central column of the imaging device 204 and counting the number of pixels on each sampled axis that have been illuminated. By comparing the diameter of the beam in both the X and Y directions, the beam diameter sensor 124 can determine whether the incident laser beam B1 is approximately circular and has the desired diameter. For example, if the number of pixels illuminated on each axis is 20 pixels, the beam will be known to have half the diameter of a beam that illuminated 40 pixels along both axes. As another example, if for any reason the beam has become elliptical, the number of pixels of the imaging device 204 illuminated along the X-axis will differ from the number of pixels illuminated along the Y-axis.

The beam diameter sensor 124 can also be used to determine the intensity profile of the laser pulses, since each pixel in the beam diameter sensor 124 can generate an output indicative of the intensity of light incident to the pixel. By comparing pixel values from radially symmetric points in the pixel array, it can be determined if an incident laser pulse or series of pulses has the desired radially symmetric intensity profile, or if the pulses have developed "hot spots" of out-range intensity values.

The output of the beam diameter sensor 124 is coupled to the computer control unit 114. The computer control unit 114 is in turn coupled to the motorized zoom lens 106, which provides control over the diameter of the laser beam B1. The computer control unit 114 is suitably programmed to vary the diameter of the laser beam as required for a particular surgical procedure. The output of the beam diameter sensor 124 as a function of beam diameter can be ascertained by standard calibration techniques.

This configuration provides positive feed-back of the beam diameter emanating from the laser unit 100. If the beam diameter sensor 124 detects an out-of-range beam (either diameter or intensity profile), the computer control unit 114 can take appropriate action, including activation of the safety shutter 120.

Figure 3A:
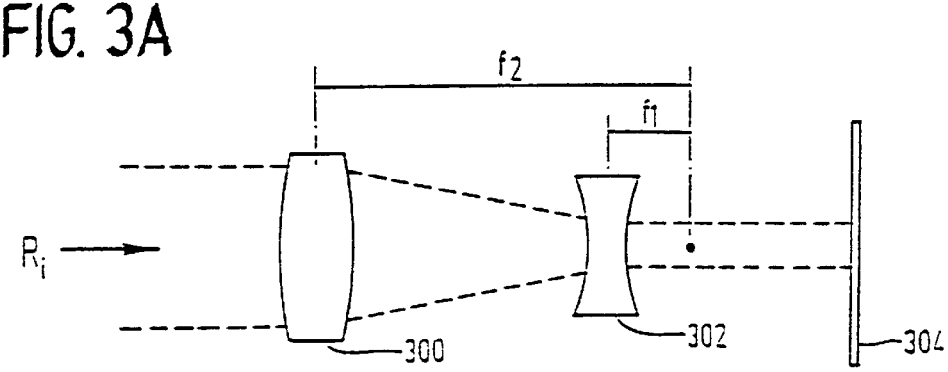
FIG. 3A is a side view of a beam location sensor, including a photo-detector, in accordance with the present invention.

To verify the X-Y scan position of the laser beam, the inventive system provides a partially transmissive beam-splitting mirror 126 that reflects part of the beam energy $R_1$ to a beam location sensor 128. Referring to FIG. 3A, the beam location sensor 128 preferably includes at least a converging (convex) lens 300 and a diverging (concave) lens 302 configured as a reducing telescope (i.e., the two lenses have a common focal point, with the focal length $f_2$ of the diverging lens 302 being greater than the focal length $f_1$ of the converging lens 300, and having optical centers aligned with the incident laser beam in its un-deflected position). The incident beam $R_I$ enters the converging lens 300 and exits the diverging lens 302. Such a configuration of lenses, while reducing the incident beam, will also increase the scan angle of the exiting beam.

The resulting increased-scan angle beam is directed to a silicon photo-detector 304 which provides a voltage reading with respect to the two-dimensional (X-Y) location of an illuminating spot at the detector surface. Such detectors are commercially available from a variety of sources, including United Detector Technologies, UDT Sensors, Hawthorne, Calif. The output of the beam location sensor 128 is coupled to the computer control unit 114.

Calibration of the voltage reading generated from the undeflected incident beam position on the detector 304 will indicate the origin OR of the laser beam in the XY-scan plane. Any deflection of the beam from the origin OR will generate voltage readings indicative of the spot on the detector 304 surface illuminated by the laser beam. These voltage readings are calibrated against the indicated location of the surgical beam as set by the computer control unit 114. During operation, the output of the beam location sensor 128 would be sampled periodically (for example, about 1,000 times per second) and compared to a prepared calibration table in the computer control unit 114 to determine if the actual beam position matches the indicated position.

This configuration provides positive feed-back of the beam position emanating from the laser unit 100. If the beam location sensor 128 detects an out-of-position beam, the computer control unit 114 can take appropriate action, including activation of the safety shutter 120.

Thus, the preferred embodiment of the inventive surgical laser apparatus provides for safe and effective surgery by continuously monitoring all aspects of the condition of the surgical laser beam S, including beam intensity, diameter, and X-Y scan position.

Eye Tracking System

Figure 4A:
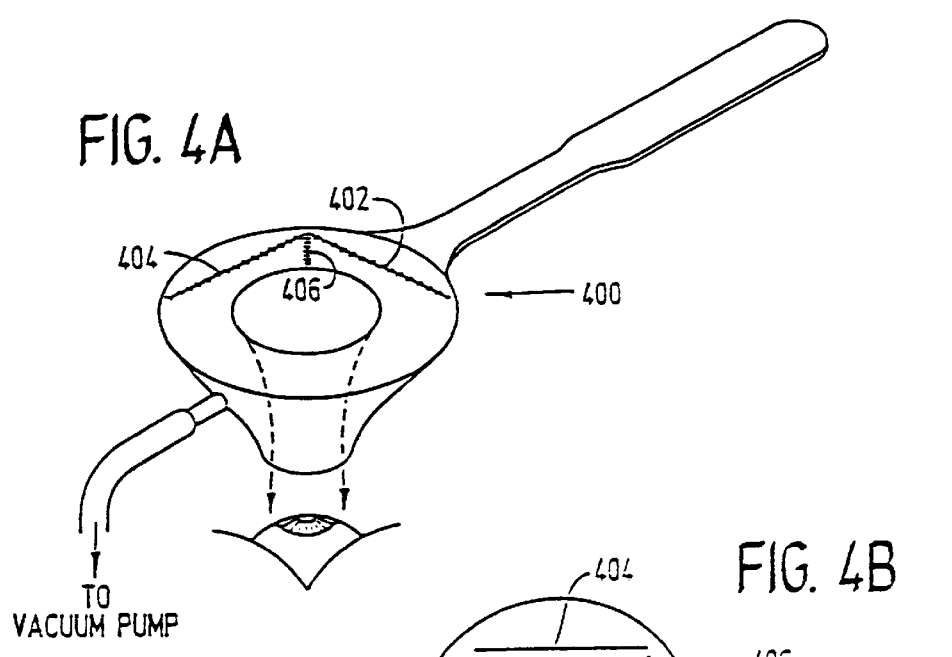
FIG. 4A is a perspective view of a vacuum ring used in conjunction with the present invention.

When using the inventive system, it is important to minimize eye movement with respect to the surgical laser beam S. Therefore, in order to locate the eye relative to the surgical laser beam S, a conventional suction ring 400, such as is shown in FIG. 4A, is used to immobilize the eye. Such devices are commercially available, for example, from Steinway Instruments of San Diego, Calif. Such suction rings are further described, for example, in U.S. Pat. No. 4,718,418 to L'Esperance, Jr.

A suction ring 400 is normally applied to the white (sclera) region of the eye and connected to a low suction pressure sufficient to clamp the ring 400 to the eye, but not so great that the cornea is distorted. The use of such a ring 400 is well-known in the art.

Despite the use of a suction ring 400 to immobilize an eye, some movement of the eye may occur (possibly through movement of the suction ring 400 itself by a surgeon). Therefore, the present invention provides an eye tracking system 130 to compensate for relative movement between the eye and the surgical laser beam S. As shown in FIG. 1, the eye tracking system 130 is placed in the path of the surgical laser beam S, preferably in close proximity to a target eye.

Figure 4B:
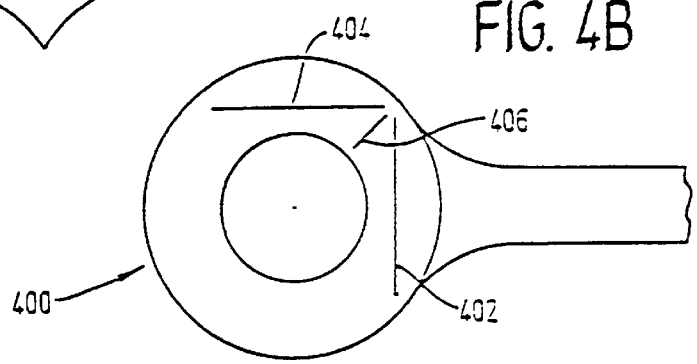
FIG. 4B is a top plan view of the vacuum ring of FIG. 4A.
Figure 4C:
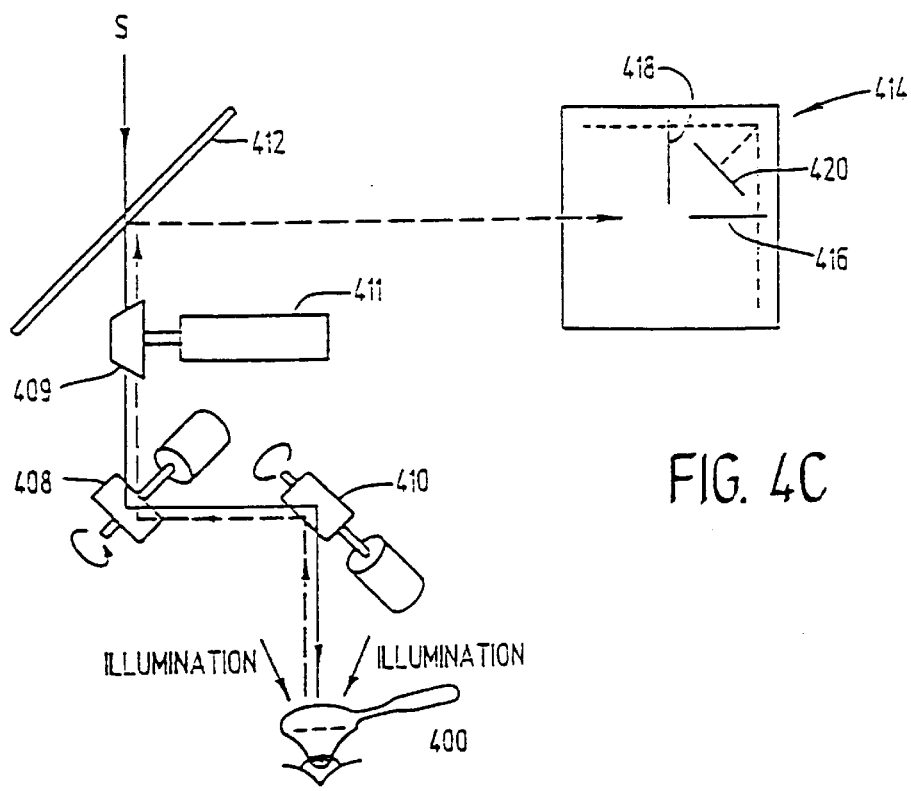
FIG. 4C is a block diagram of an eye tracking system in accordance with the present invention.

Referring to FIGS. 4A, 4B, and 4C, a conventional suction ring 400 is provided with distinct marks 402, 404, 406 on the back of the ring facing the surgical laser system (see particularly FIG. 4B). The marks may or may not be subdivided by cross-marks, for visual reference by a surgeon. In the preferred embodiment, the marks include an X-axis 402, an orthogonal Y-axis 404, and a radial axis 406. The marks are preferably made to be highly reflective of broadband illuminating light, and the background of the suction ring 400 is preferably flat black to enhance contrast and minimize extraneous reflections.

The eye tracking system 130 includes a pair of steering mirrors 408, 410 each comprising a reflector mounted on a galvanometer scanner or similar actuator device which is controllable by a computer, and a rotational control device consisting of a dove prism 409 mounted with its rotational axes aligned with the surgical laser beam S (see FIG. 4C). A motorized drive unit 411 is attached to a gear or bell drive designed to control the rotation of the dove prism 409. As is known, rotation of a dove prism will cause an exit beam to be rotated with respect to an incident beam. The steering mirrors 408, 410 are mounted with their rotational axis orthogonal to each other and situated such that the surgical laser beam S enters the eye tracking system 130, passes through the dove prism 409, bounces off of a first steering mirror 408 to the second steering mirror 410, and thence to a target cornea. The steering mirrors 408, 410 and the dove prism 409 therefore provide a means to "bias" the surgical laser beam S to compensate for movement of the eye relative to the surgical laser beam S.

Control of the steering mirrors 408, 410 and the dove prism 409 is provided by reflecting the image of the illuminated marks 402, 404, 406 on the suction ring 400 back up the optical path of the surgical laser beam S to a partially transmissive beam-splitting mirror 412, which directs the reflected image onto a tracking sensor 414 (other elements, such as focussing optics, may be included in the tracking sensor 414). In the preferred embodiment, the tracking sensor 414 includes three linear array sensors 416, 418, 420. Each linear array sensor 416, 418, 420 corresponds to one of the marks 402, 404, 406 on the suction ring 400, and is oriented orthogonally to the corresponding mark. In the preferred embodiment, each linear array sensor may be a linear reticon with about 1,024 or more sensing elements per inch. Such linear reticons are available commercially, such as from EG&G, Princeton, N.J.

Because of the orthogonal orientation of each mark 402, 404, 406 with respect to a corresponding linear array sensor 416, 418, 420, any movement of the suction ring 400 will result in a relative displacement of the reflected image of one or more of the marks 402, 404, 406 with respect to the corresponding linear array sensor 416, 418, 420. Such movement can be easily detected by comparing a stored initial position of each mark 402, 404, 406 with the position of each mark determined by periodically scanning the output of each linear array sensor 416, 418, 420. Because of the relative orientations of the marks 402, 404, 406, translational movements of the suction ring 400 in the X and Y directions, as well as rotational movements, can be detected. The output of the tracking sensor 414 as a function of the positions of the reflected marks 402, 404, 406 can be ascertained by standard calibration techniques.

The eye tracking system 130 may be provided with its own feedback control system to adjust the positions of the steering mirrors 408, 410 and the dove prism 409 to compensate for detected relative motion of the eye with respect to the surgical laser beam S. Alternatively, the eye tracking system 130 may be coupled to the computer control unit 114. Control of the eye tracking system 130 through the computer control unit 114 is preferred, since the computer control unit 114 can activate the safety features of the inventive system (e.g., the safety shutter 120) if the target eye is improperly aligned with the surgical laser beam S or if a failure occurs in the eye tracking system 130.

In either case, the output of the tracking sensor 414 would be monitored, and the positions of the steering mirrors 408, 410 and the dove prism 409 adjusted accordingly. In compensating for relative eye movement, it is preferable to first correct for the reflected image position of the mark 402, 404, 406 having the greatest deviation.

The inventive eye tracking system thus provides a means of improving the accurate placement of laser pulses to the cornea. By using distinct marks 402, 404, 406 on the suction ring 400, the invention provides more precise detection of relative movement of the eye compared with systems using a natural indicator, such as the pupil or the sciera of the eye (which, in any case, could not indicate rotational movement).

Method of Depositing Laser Pulses

Figure 3B:
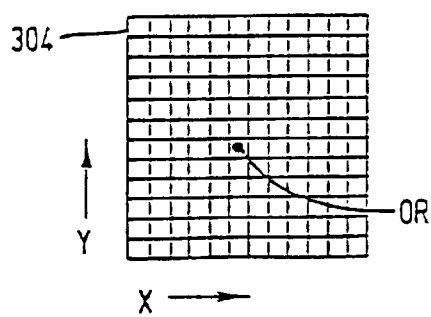
FIG. 3B is a front view of the photodetector of FIG. 3A.

Another problem addressed and solved by the present invention is the proper deposition of laser beam energy on the cornea to ablate tissue to any desired depth while leaving an optically-smooth cornea surface after the laser surgery. In the prior art, it has been known to apply a laser beam in a raster scan or a circular or spiral scan pattern over the area of the cornea where tissue is to be removed (see, for example, FIGS. 3 and 4 of U.S. Pat. No. 4,718,418 to L'Esperance, Jr.). A problem with such patterns when used with prior art laser systems is that such systems ablate tissue to a depth of about 0.3 to 15 microns or more per laser pulse. A typical procedure for laser etching of the cornea must remove from about 0.2 microns or less, up to about 50 microns of tissue. Since it is essentially impossible to accurately place each and every pulse so that it is perfectly contiguous to a neighboring pulse, ridges or grooves in the corneal surface of the same magnitude will result from the imperfect pattern of deposition of laser pulses. Accordingly, post-operative visual acuity will be reduced because of light scattering from the inhomogeneity of the tissue at the uneven interface.

Another problem of the prior art, particularly with excimer lasers, is that the beam intensities used have principally had a "top hat" intensity profile of the type shown in FIG. 6A. Such an intensity profile will result in essentially a mirror-image ablation profile, as shown in FIG. 6B.

Attempt have been made to avoid the sharp edges caused by a "top hat" intensity profile by adapting instead a radial profile having a Gaussian intensity profile (intensity= $e^{-2(r/\omega)^2}$, where $\omega$ is the beam waist) (curve 600 in FIG. 6C) or a super-Gaussian intensity profile, which is a slightly modified Gaussian curve with a lesser gradient at the center (curve 602 in FIG. 6C), resulting in correspondingly shaped tissue ablation profiles, as shown in FIG. 6D.

To overcome the problem of haze-inducing ridges and grooves, the prior art has attempted to overlap Gaussian or super-Gaussian beam intensity profiles to generate a smoother average etch profile. For example, as shown in FIG. 6E, overlapped Gaussian beam intensities result in an average beam intensity equivalent to that shown in FIG. 6F, which results in a corresponding mirror-image ablation etch profile as shown in FIG. 6G.

A problem with this approach is that, during photoablation, vaporized tissue material is expelled from each tissue site ablated by a laser pulse (the expelled tissue is known as "plume"). It is known that such expelled debris can scatter photons in an incoming laser beam (this is known as "shadowing"). As should be expected, this phenomena reduces the intensity of the beam. Thus, when laser pulses are overlapped as described above, a prior adjacent pulse will generate a plume that partially shadows or obscures the incoming laser beam of a subsequent adjacent laser pulse, causing non-uniformity of tissue ablation and hence irregularities on the cornea surface.

An additional problem of prior art overlapped laser deposition patterns is that such patterns are repeated in such a manner that significant-sized ridges and grooves are still formed between pulse centers.

The solution of the present invention to the problems of the prior art laser deposition patterns is to use a Gaussian, or, preferably, a super Gaussian intensity profile for each laser pulse, and to deposit the pulses in a plurality of layers, each layer having a regular geometric pattern. The origin of each layer of the pattern is off-set by a specific distance in either the X or Y dimension from each prior, or subjacent, layer. The inventive pattern avoids the problem of plume by not overlapping the laser pulses of any one layer, and overcomes the problems of prior art ridge and groove formation by uniformly depositing laser energy over the surface to be etched. Because of the shallow etch depth of each laser pulse of the present invention (about 0.2 microns or less), etching can be stopped essentially at any point in the ablative process while leaving an optically smooth cornea surface.

Figure 7A:
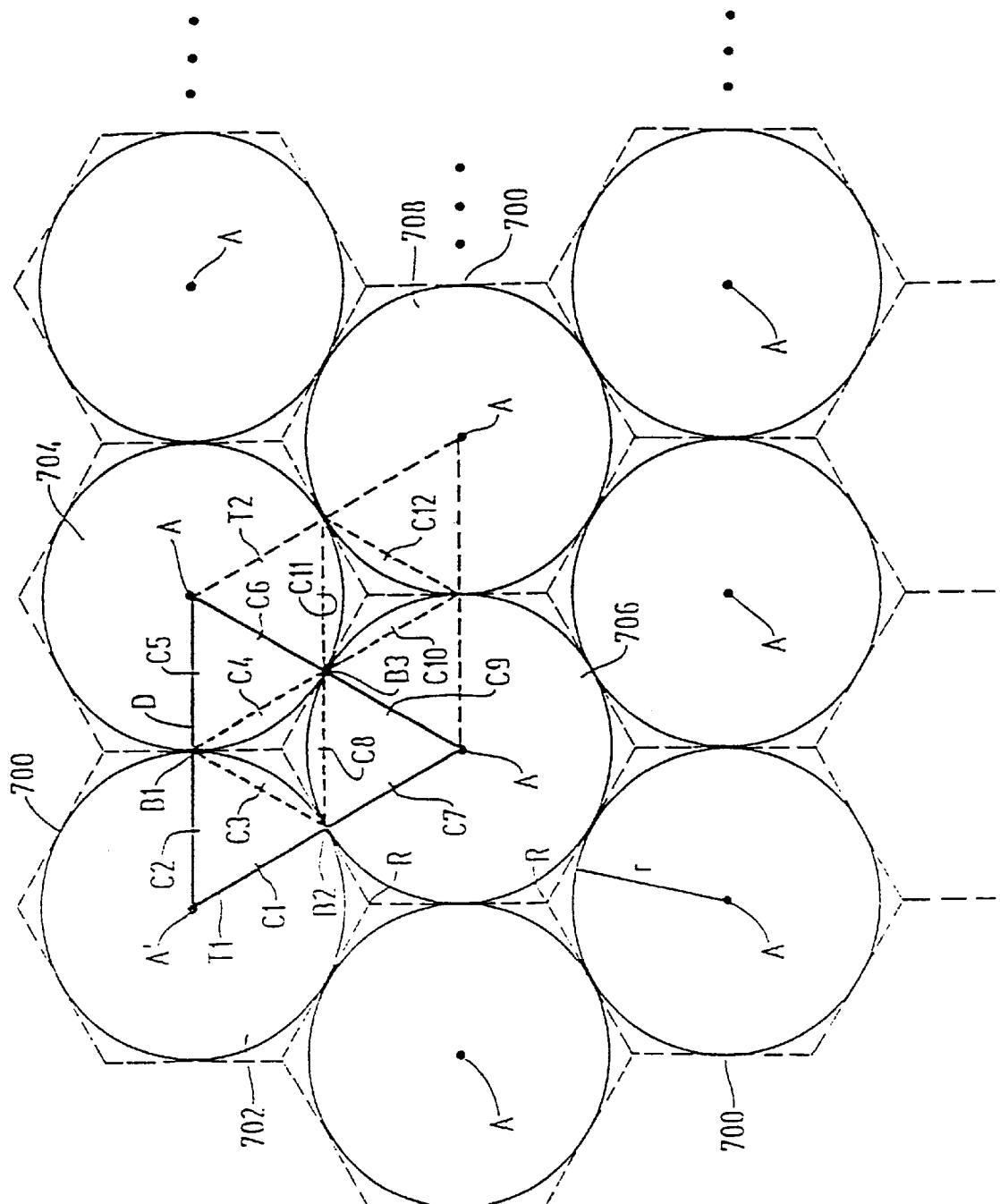
FIG. 7A is a diagram of a first level pattern used in scanning a target with the present invention.

Referring to FIG. 7A, shown is a part of a first level scan pattern, comprising a single etch layer. In the preferred embodiment, each laser pulse creates an etch profile with an approximately circular cross-section with a radius r, which may typically range from about 0.02 mm to about 0.5 mm. The scan pattern programmed into the laser unit 100 lays down a pattern of pulses in a hexagonally-packed array of the type shown in FIG. 7A. That is, the center A of each circular cross-section etch circle 700 of radius r is spaced a distance D, equal to 2r, from the center A of each other etch circle 700. As is known, the pattern resulting from this simple criteria is a hexagonally-packed array of circles (the dotted hexagons shown in FIG. 7A are for purposes of illustrating the packing pattern, and do not form any part of the etch profile).

While it is preferred that the etch circles be non-overlapping and contiguous, the invention encompasses slight overlapping and/or spacing of etch circles due to tolerance limits on positioning etch circles with a practical laser apparatus.

A benefit of the hexagonally-packed array of etch circles is that the pattern is simple to program into the scanning control system of the laser unit 100 as a modified raster scan. If etch circle 702 having center A' is considered to be the origin for the initial first level pattern, the laser unit 100 need only move the laser beam in the X direction a distance of D to the center A for the next etch circle 704. Additional etch circles are created in the same manner for the first row, until the opposite edge of the area to be ablated is reached. Such precision of placement of etch circles is made possible by the highly accurate X-Y positioning capability of the laser unit 100, particularly when used in conjunction with the eye-tracking system described above.

After the first row of etch circles is completed in the same manner, the laser beam is moved down in the Y direction a distance of about 0.866 D (one-half the square root of 3 times D, representing the vertical distance between centers of adjacent rows), and left or right along the X direction by ½ D (representing the horizontal distance between centers of adjacent rows). The beam is then either scanned backwards, or returned to the original "edge" of scanning and scanned forwards in the same manner as the first row. Each subsequent row is created in the same manner, until the bottom edge of the area to be ablated is reached, thus completing the first level layer.

Although a regular order of etch circle deposition is preferred for ease of programming the laser unit 100, the accurate X-Y positioning capability of the laser unit 100 permits the etch circles for a particular layer to be deposited in any order, including randomly.

A characteristic of the first level pattern shown in FIG. 7A is that no circular etch substantially overlaps any other circular etch. Consequently, the problem of plume is minimized. While laying down only the first level pattern shown will result in ridges in the gaps between etch circles, because of the shallow etch depth used, the crest-to-trough distance of any ridge area R to the center A of any etch circle 700 will be at most about the same as the etch depth of a single etch (about 0.2 microns or less).

After laying down the initial first level pattern shown in FIG. 7A, the inventive method preferably lays down a second level pattern, comprising three etch layers. Each second level etch layer is an exact replica of the single etch layer of the first level pattern (i.e., an hexagonally-packed array of etch circles of radius r). However, the origin of each of the three layers with respect to each other and to the first level layer is unique. In order to minimize ridges and grooves in the etched cornea, each layer of the second level pattern is offset from the single layer of the first level pattern to even-out the distribution of laser energy across the cornea. This concept of off-setting subsequent layers in exact relationship with respect to an initial layer is in contrast to the prior art, which typically repeats the etching process by sweeping the laser beam across the ablation zone without reference to the exact location of each of the laser pulses.

More specifically, the origin of the first layer of the second level is set at point B1 (or an equivalent point; see below) of FIG. 7A, which is one-half the distance D between the first level origin A' of etch circle 702 and the center of the adjacent etch circle 704. Using point B1 as an origin, the laser unit 100 is programmed to lay down an entire array of etch circles covering the area to be ablated, using the same rules for changing beam location as described above for the first level etch layer.

Similarly, the origin of the second layer of the second level is set at point B2 (or an equivalent point; see below) of FIG. 7A, which is one-half the distance D between the first level origin A' of etch circle 702 and the center of the adjacent etch circle 706 in the next row. Using point B2 as an origin, the laser unit 100 is programmed to lay down an entire array of etch circles covering the area to be ablated, using the same rules for changing beam location as described above for the first level etch layer.

Lastly, the origin of the third layer of the second level is set at point B3 (or an equivalent point; see below) of FIG. 7A, which is one-half the distance D between the center of etch circle 704 and the center of the adjacent etch circle 706 in the next row. Using point B3 as an origin, the laser unit 100 is programmed to lay down an entire array of etch circles covering the area to be ablated, using the same rules for changing beam location as described above for the first level etch layer.

Figure 7B:
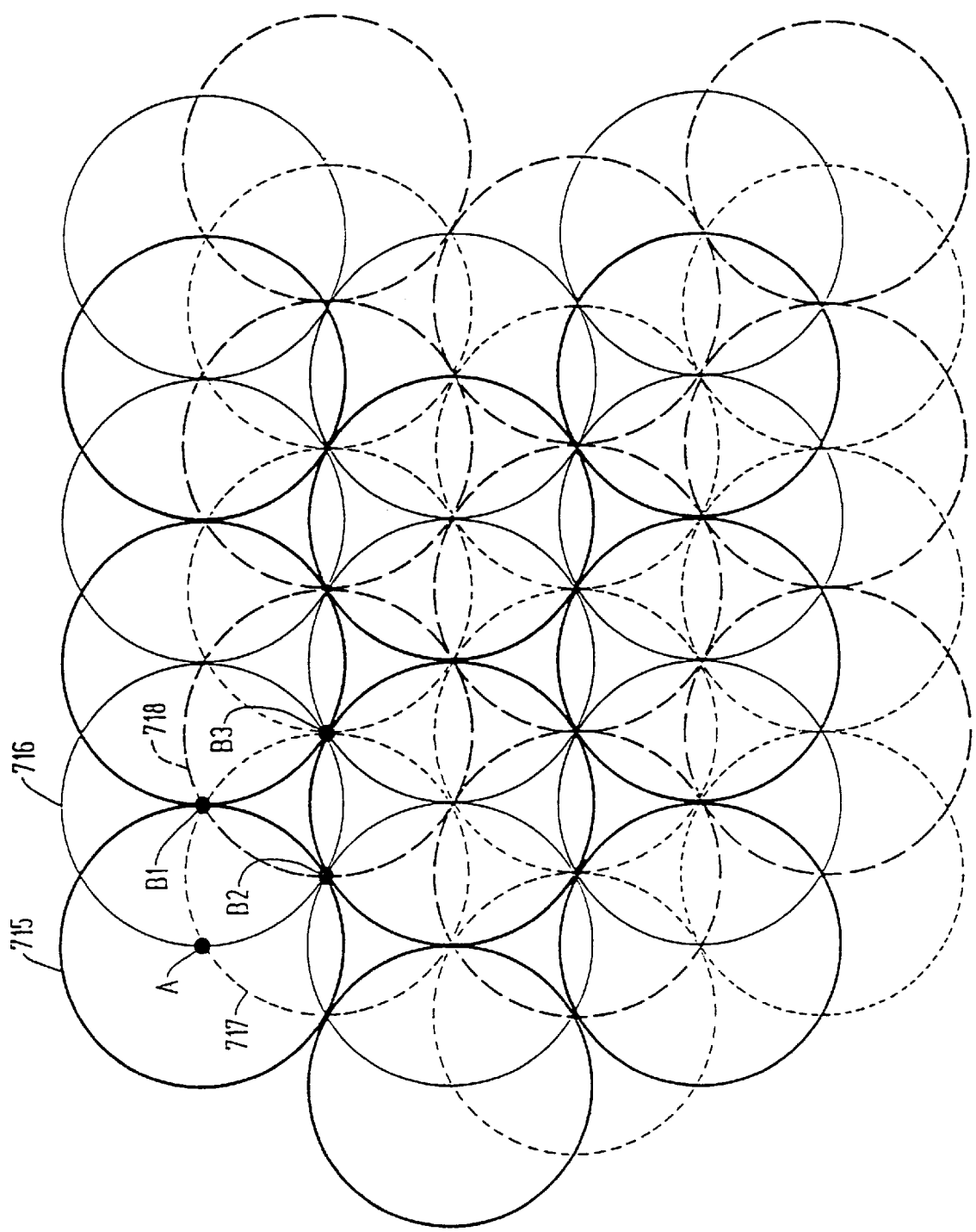
FIG. 7B is a diagram of a second level pattern used in scanning a target with the present invention.

The resulting etch pattern for the second level will resemble the pattern shown in FIG. 7B, which shows the first level centered at A' as thick-lined circles 715, the first layer centered at point B1 as solid circles 716, the second layer centered at point B2 as dotted circles 717, and the third layer centered at point B3 as dashed circles 718. If desired, the level one and two etch patterns may be repeated as needed to obtain the desired amount of ablation.

Although the second level comprises three layers, all three layers need not be completed. Further, the first layer of the second level can be started with its origin at any of the three points B1, B2, or B3, since all of these points are geometrically equivalent. More generally, equivalents of these three offset points exist throughout the grid of centers A defined by the initial first level layer. Thus, any equivalent offset point in the second level may be selected as the origin of one of the three layers comprising the second level. The overall etch profile (determined as described below) determines which of the equivalent second level offset points will be selected to achieve maximum ablation where required in the surface being etched, and whether the desired degree of smoothness of finish requires completion of each of the second level layers. However, to ensure evenness of etching, it is generally desirable to complete all layers of the second level before additional levels of etching commence.

As an alternative way of modelling the first and second levels, they may instead be considered as a single etch pattern "unit" comprising four etch layers arranged to overlap in the manner shown in FIG. 7B.

If desired, further levels of etch patterns could be generated in a similar fashion by repeating levels one and two, using new origins. A characteristic of the geometry of an hexagonal packing array lends is that it lends itself to creation of repeating regular patterns. For example, referring to FIG. 7A, the origins B1, B2, and B3 for the second level etch layers comprise the midpoints of a triangle T1 connecting the centers of etch circles 702, 704, and 706. A second triangle T2 can be created by connecting the centers of etch circles 704, 706, and 708 (shown in dotted outline in FIG. 7A). These two triangles comprise a symmetrical unit that is repeated throughout the pattern of centers A defined by the initial first level pattern. Moreover, by connecting adjacent midpoints, each of the triangles T1 and T2 can be subdivided into four smaller, equal-sized triangles, as shown in FIG. 7A. The midpoints of each sub-triangle in a T1-T2 unit not shared with a similar T1-T2 type unit comprise twelve offset points C1–C12 that have equivalents throughout the grid of centers A defined by the initial first level layer.

Each of these equivalent offset points C1–C12 can be used as an origin for a set of level one and level two etch patterns. That is, taking point C11 as an example, C11 can be selected as the center of a level one pattern. The level one pattern centered at C11 then defines a new grid for a corresponding level two pattern. Similarly, point C2 could then be selected as the center of another level one pattern. The level one pattern centered at C2 then defines a new grid for a corresponding level two pattern.

With such third level equivalent offset points defined, any of them may be selected as the origin of one of the 48 layers (12 level one/level two sets) comprising the third level. The overall etch profile (determined as described below) determines which of the equivalent third level offset points will be selected to achieve maximum ablation where required in the surface being etched, and whether the desired degree of smoothness of finish requires completion of each of the third level layers. However, to ensure evenness of etching, it is generally desirable to complete all layers of the third level before additional levels of etching commence.

The process of defining subsequent levels may be extended as necessary, by defining equivalent offset points based on repeating geometrical units determined by the grid of centers A defined by the initial first level layer. The general rule is to divide a previous level into additional triangles based on the grid defined by the initial first level layer. This is done by connecting three adjacent origins to form such triangles, and then using the midpoints of such triangles as new origins.

The extent of improvement on the surface smoothness by the precise positioning of multiple layers of etch profile is illustrated in the following: Using a Gaussian laser beam profile as an example, and setting the laser energy density at the peak of the laser pulse to be four times the ablation threshold, the surface smoothness can be characterized in relation to the maximum etch depth of a single laser pulse. For example, after applying the first level etch pattern as described above using a Gaussian intensity profile, the maximum crest-to-trough distance of the etch patterns anywhere within the boundaries of the etched area will of course be 100% of the maximum crest-to-trough distance of a single etch circle. By applying just two levels of etch patterns as described above using a Gaussian intensity profile, the maximum crest-to-trough distance of the overlapped etch patterns anywhere within the boundaries of the etched area will be at most about 53% of the initial first level pattern alone. By applying three levels of etch patterns using a Gaussian intensity profile, the maximum crest-to-trough distance of the overlapped etch patterns anywhere within the boundaries of the etched area will be at most about 20% of the initial first level pattern alone. Since the crest-to-trough distance for the initial first level pattern is about 0.2 microns or less, and preferably about 0.05 microns or less, even the second level pattern may be sufficient to achieve the desired result.

Figure 7C:
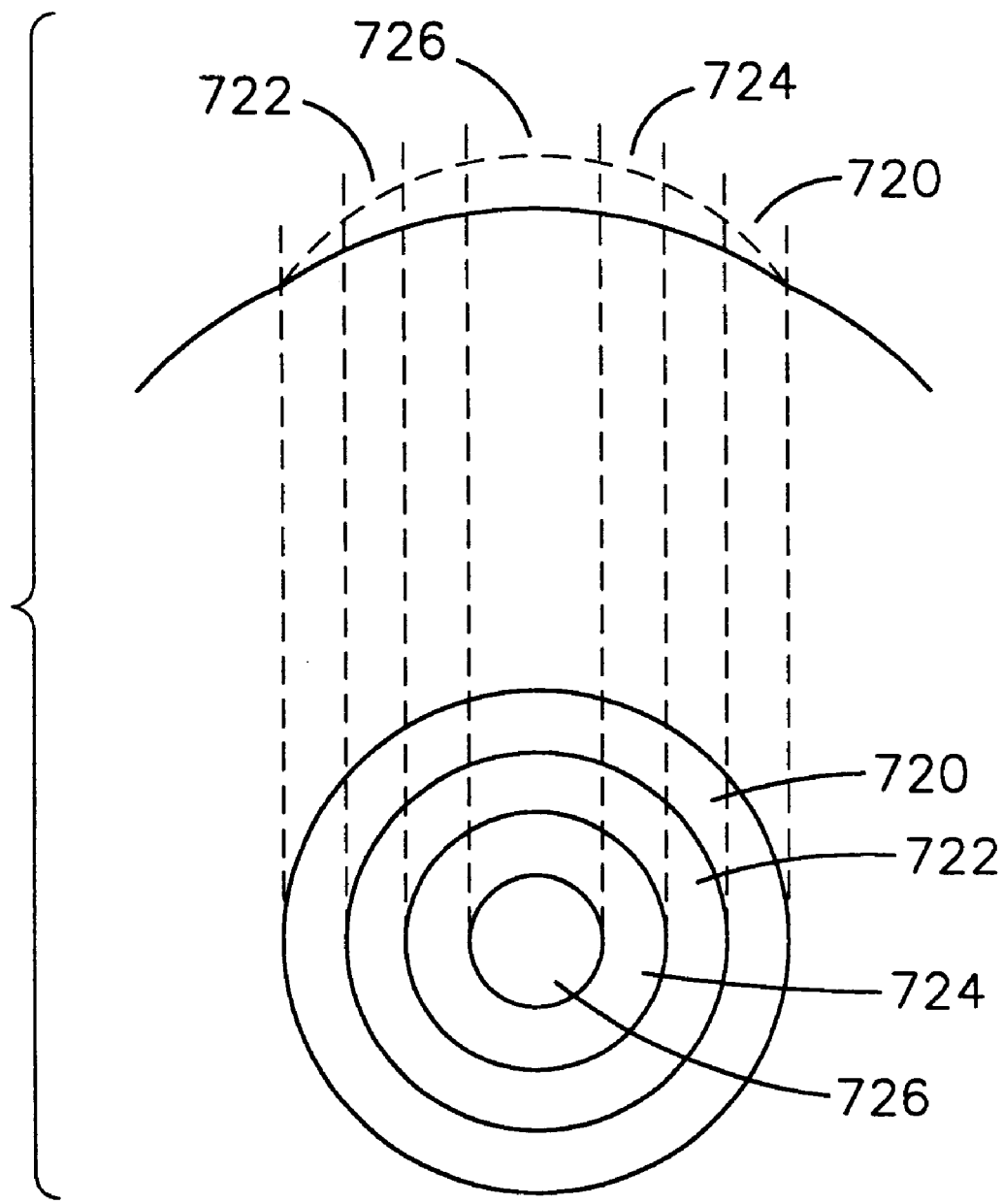
FIG. 7C is a top and side view of a pattern of concentric circles etched on a cornea using the etch deposition patterns of the present invention.
Figure 7E:
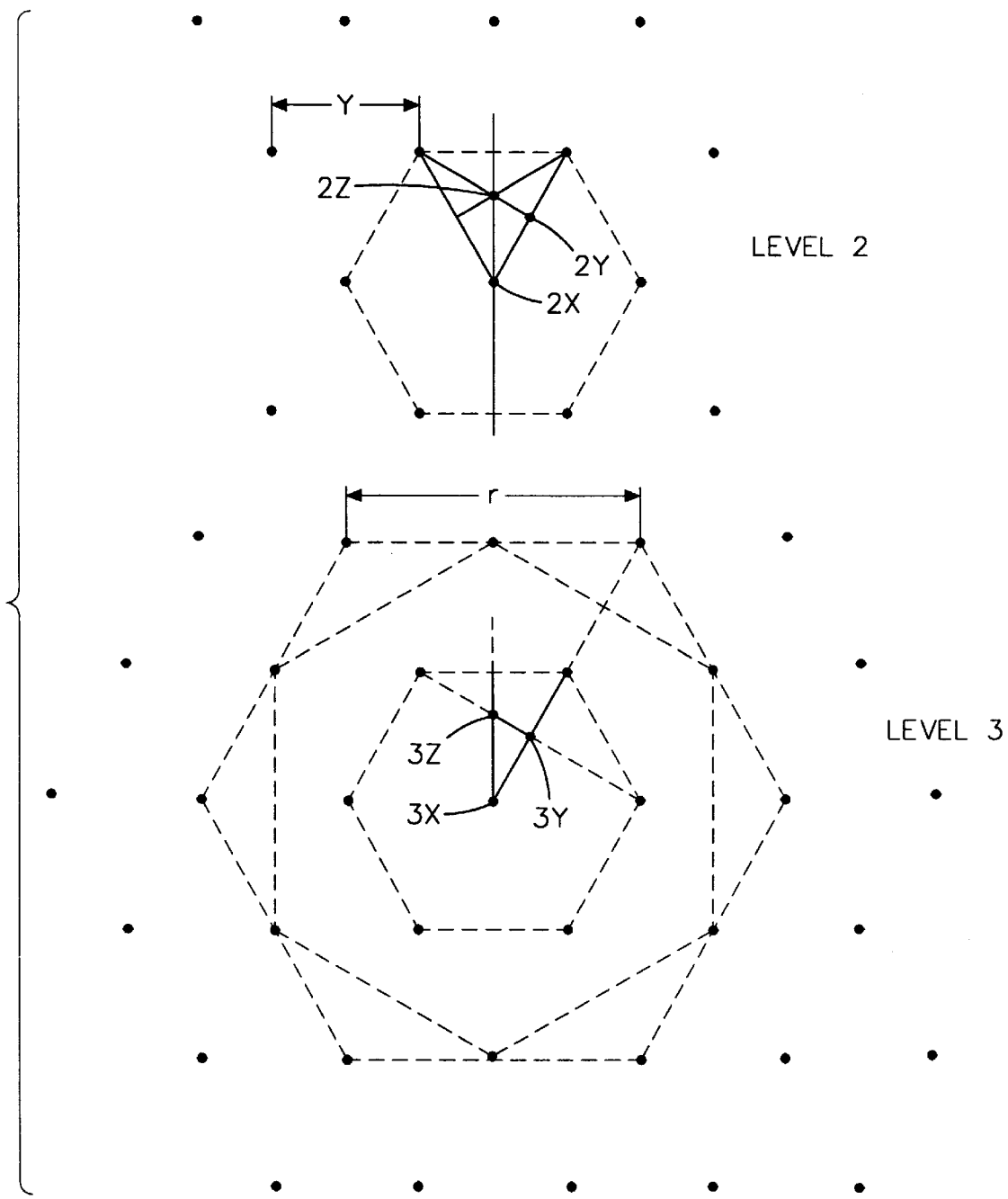
FIG. 7E is a diagram showing the measurement axes used to compute the level two and level three crest-to-trough distances of FIG. 7D.

This analysis is graphically presented in FIG. 7D, which shows a set of graphs showing the cumulative crest-to-trough distances of level one, level two, and level three etch patterns in accordance with the present invention. The Y-axis of each graph shows the cumulative etch depth in units of the maximum etch depth of a single laser pulse. The X-axis shows etch depth as a function of the distance from an etch circle center out along one of the three symmetry axes for an hexagonal array. FIG. 7E shows the measurement axes used to compute the level two and level three crest-to-trough distances of FIG. 7D. The notation for the end-points of the X-axis of FIG. 7D corresponds to the notation for the measurement points shown in FIG. 7E.

The regular characteristics of the inventive deposition system are useful when etching the cornea in a "stepped pyramid" fashion (in terms of laser pulse count), with fewer etch circles deposited towards the periphery of the cornea and more etch circles deposited towards the center. As shown in FIG. 7C, the resulting overall etch pattern typically resembles concentric circles (although other shapes are possible). When etching from the outer edge to the center, the entire cornea is etched to the diameter of ring 720, using the etch patterns discussed above. Using the original grid of centers A from the very first level, a new origin at an equivalent offset point within ring 722 is chosen when the tissue in ring 720 has been etched to the desired degree. Etching continues over the entire cornea encompassed within the diameter of ring 722. Again, using the original grid of centers A from the very first level, a new origin at an equivalent offset point within ring 724 is chosen when the tissue in ring 722 has been etched to the desired degree. Etching continues over the entire cornea encompassed within the diameter of ring 724. The process continues in similar fashion until the center ring 726 is etched to the proper depth. (Note that the diameter of the laser pulses may be made smaller in the inner rings to provide a finer etching grid, in which case, a new initial first level pattern defining such a grid may be laid down and used in determining equivalent offset points for subsequent levels).

As should be clear by considering FIG. 7C, the etch process could be done in reverse order, with center ring 726 etched first, then the area encompassed within the diameter of ring 724, then the area encompassed within the diameter of ring 722, and finally the area encompassed within the diameter of ring 720.

Wavelength Converter Means

As described above, the inventive system includes at least one wavelength converter to alter the wavelength of the initial laser beam B1 to the desired wavelength in the range of about 198–215 nm.

Figure 5A:
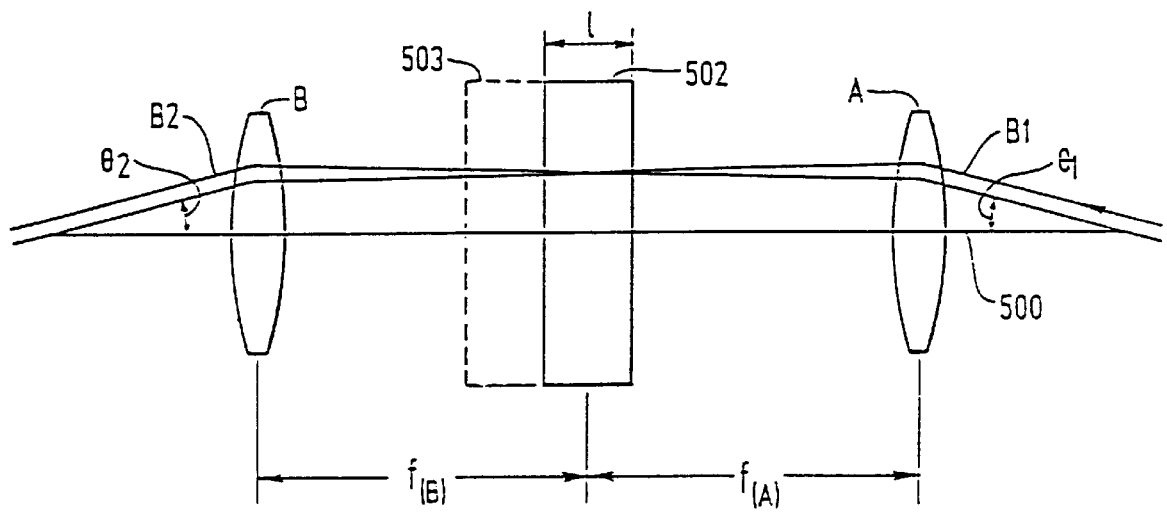
FIG. 5A is a block diagram of a first embodiment of a wavelength converter in accordance with the present invention.

A first example of one wavelength converter is shown in FIG. 5A. In FIG. 5A, the initial laser beam B1 emerging from the laser unit 100 is shown to have been scanned at an incident angle $\theta_1$ from its central position 500, which is defined as the center position of the total scan angle to be covered for an intended surgical operation. Generally, the laser beam is scanned in two dimensions, and hence two angular positions are needed to specify each unique beam position. In the preferred embodiments shown in FIGS. 2A and 2B, the optical system is spherically symmetric. Thus, only one of the incident scan angles will be illustrated in the following discussion without loss of generality.

In FIG. 5A, a convex lens A is located at a distance f(A), the focal length of lens A from the pivot point of the scanned laser beam B1. In the illustrated embodiment, the pivot point is inside the scanner-amplifier unit 104, at an equivalent position of the scan mirror near the exit dielectric mirror, as described below. A nonlinear optical crystal 502 is chosen such that phase matching angles exist with a proper crystal orientation so that a fundamental laser wavelength within a range of about 790–860 nm can be converted to its second harmonic at a wavelength in the range of about 395–430 nm. One possible such crystal is beta-$Ba_2BO_4$ (beta barium borate). This crystal has a phase matching angle at about 26–30° for the wavelength range stated above, in type I phase matching conditions. The nonlinear crystal 502 is positioned at a distance f(A) from the lens A. The incident laser beam B1 is weakly focused at the crystal 502 with a choice of a long focal length for lens A. Another convex lens B located at the focal length f(B) of lens B from the crystal 502 re-collimates the beam into an emergent laser beam B2. Preferably, both lenses A and B are coated for maximum transmission at laser lengths for which each transmits.

The dimensions of the nonlinear crystal 502 are chosen such that the surface area where the incident laser beam B1 enters the crystal 502 is sufficiently large that the laser beam will not be cut off at the extremity of its scan angles. The length 1 of the crystal 502 is such that the conversion efficiency is to be optimized, in consideration of the walk off between the fundamental and the second harmonic beam, the group velocity dispersion, and the spectral bandwidth for the short duration laser pulses. The entrance surface of the nonlinear crystal 502 is coated for maximum transmission of the fundamental wavelengths and the exit surface is coated for maximum transmission of the second harmonic wavelengths.

The optical arrangement of the present embodiment of the wavelength converter offers several additional advantages: the scan angle $\theta_1$ of the incident laser beam B1 can be magnified or reduced by choosing the proper focal length for the lens B. If f(b) is smaller than f(A), the beam scan angle $\theta_2$ in FIG. 5A will be magnified by a factor f(A)/f(B). On the other hand, if f(B) is larger than f(A), the beam scan angle $\theta_2$ will be reduced by a factor of f(A)/f(B).

It is important to note that the laser beam, which subtends an angle $\theta_1$ from the central position 500, becomes parallel to the central position 500 after passing through lens A. Therefore, lens A provides two improvements in the harmonic conversion process: the laser photon density at the non-linear crystal 502 is increased due to the smaller beam area, and the laser beam orientation incident at the non-linear crystal 502 is maintained at all scan angles, thereby maintaining the phase matching conditions of the beam while it is being scanned.

Another advantage of the embodiment shown in FIG. 5A results from the change of location of the incident laser beam B1 through the nonlinear crystal 502 as the beam is scanned. Within the nonlinear crystal 502, a small amount of the laser beam is absorbed, resulting in a thermal gradient across the beam cross-section. This temperature variation at different portion of the incident beam B1 degrades the phase matching conditions, and places a limit on the conversion efficiency of the harmonic generation process. By moving the beam over an area during scanning, the thermal energy is effectively distributed over that area, and the average power loading in the crystal 502 is effectively reduced. If the area is sufficiently large, the laser pulses becomes non-overlapping. Reduction of pulse overlapping also results in an improved crystal damage threshold. For a laser beam with a high repetition pulse rate, if the laser beam is stationary, as in the prior art, there is a time delay requirement, so that the effect of a laser pulse through a nonlinear crystal is allowed to dissipate before the next laser pulse arrives. This requirement places an upper limit on the repetition rate at about 10,000 pulses per second. The present invention overcomes the above prior art limitations, and provides an improved method of laser wavelength conversion to attain a higher conversion efficiency and a higher crystal damage threshold by scanning the laser beam across the nonlinear crystal 502. With the present invention, the repetition rate of the surgical beam can be extended to over 50,000 pulses per second.

Figure 5B:
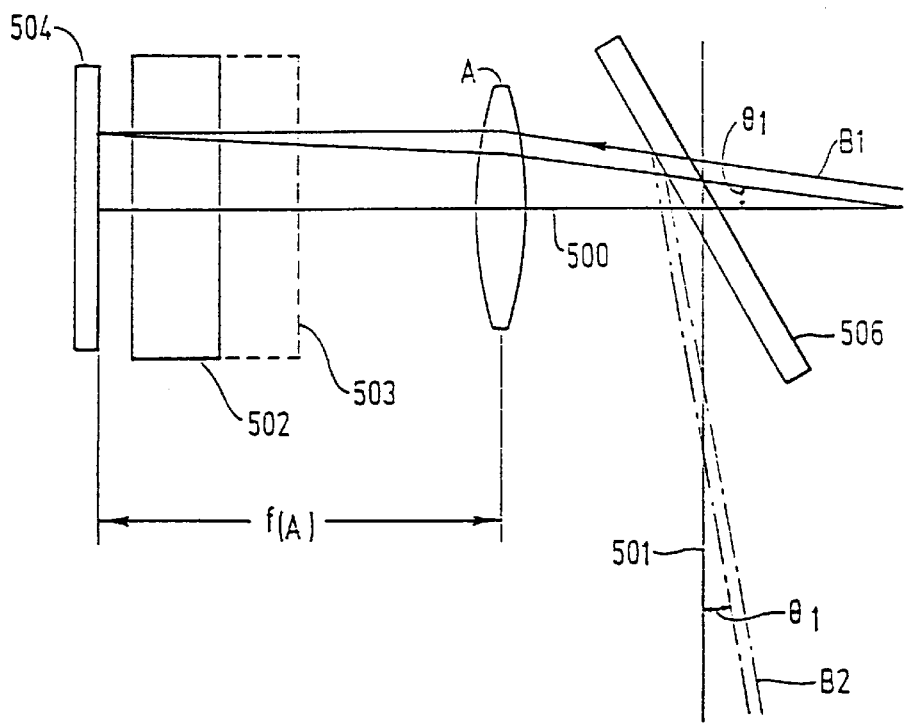
FIG. 5B is a block diagram of a second embodiment of a wavelength converter in accordance with the present invention.

A second example of a wavelength converter is shown in FIG. 5B. In this embodiment, lens A and the nonlinear crystal 502 are similarly located as specified for FIG. 5A, except that the crystal 502 is positioned slightly closer to lens A. A high reflective mirror 504 is located at a distance f(A) from lens A. The reflective mirror 504 has the characteristics of being highly reflective at the fundamental and the second harmonic wavelengths of the incident laser beam B1. A partially-transmissive beam-directing mirror 506 is included in the beam path, and is set at about 45° from the laser beam central position 500. The beam-directing mirror 506 is coated with dielectric thin films for high transmission of the fundamental wavelength, and high reflection of the second harmonic wavelength at near 45°. An incident laser beam B1 at an angle $\theta_1$ with the central position 500 passes through the beam-directing mirror 506, and is focussed by lens A on the nonlinear crystal 502. The beam is then reflected at the reflective mirror 504, passes through the crystal 502 a second time, and re-traces its beam path through the lens A. The second harmonic portion of the beam is then reflected by the 45° beam-directing mirror 506. The exit beam is now at an angle $\theta_1$ from a rotated central position 501, which is at two times the exact angle of the beam-directing mirror 506, and thus is about 90° with respect to the central position 500.

The advantage of the structure and method shown in FIG. 5B is that the non-linear crystal 502 is used twice by the fundamental beam. This method can almost double the conversion for the case of low conversion efficiency, in the case where the fundamental beam intensity is not significantly depleted in its first passage (e.g., when the wavelength conversion efficiency is less than about 30–40%).

In the present embodiment, the residual laser photons of the initial laser beam B1 will not be used and may be filtered out by a dielectric coated mirror which has bandpass characteristics of high transmission at the second harmonic wavelengths of about 395–430 nm and blocking at the fundamental wavelengths of about 790–860 nm. Alternatively, the fundamental and the second harmonic waves can be separated spatially using dispersive optical elements, such as a high optical index prism or an optical grating. The filtering optics (not shown) can be placed in the beam path after the beam emerges from the first wavelength converter 108.

As noted above, after emerging from the first wavelength converter 108 (see FIG. 1), the second laser beam B2 has a wavelength in the range of about 395–430 nm. To attain the preferred operating laser wavelengths of 198–215 nm, the laser beam is directed into a second wavelength converter 110.

The optical arrangement of the second wavelength converter 110 is almost identical to that of the first wavelength converter 108, which is illustrated in FIGS. 5A and 5B. The main difference between the two converters 108, 110 is in the optical crystal 502. For wavelength conversion from about 395–430 nm to about 198–215 nm, the preferred nonlinear optical crystal is again beta-$Ba_2BO_4$ (beta barium borate). The operating conditions are different in that the phase matching angles are at or close to 90° for type I phase matching. The optical faces of the crystal 502 are to be coated for maximum transmission at the front surface for the fundamental wave where the laser beam enters the crystal 502, and for maximum transmission at the second harmonic wave on the exit face. The optical characteristics of beta-$Ba_2BO_4$ crystals impose a lower limit of the converted wave at about 200 nm for appreciable conversion efficiency.

The third laser beam B3 emerging from the second wavelength converter 110 has a residual wavelength of about 390–430 nm. A wave filter means consisting of dispersive prism or optical gratings can be used to spatially separate the 200 nm wavelengths from the 400 nm wavelength contents. The wave filter (not shown) can be placed anywhere in the laser beam path after the second wavelength converter.

The two-step wavelength conversion process described above can also be consolidated such that the fundamental wavelength can be converted into its fourth harmonic with a single optical arrangement. As illustrated in FIGS. 5A and 5B, first and second nonlinear optical crystals 502, 503 (shown in dotted outline) are placed in close proximity and are at the beam waist of the mildly focussed incident laser beam. The first crystal 502 is cut and oriented for phase match conditions to generate the second harmonic wave. The first crystal 502 is used to convert the fundamental wave into its second harmonic wave, and has a function as described above for the single-crystal embodiment of the first wavelength converter 108. For this purpose, in the configuration shown in FIG. 5A, the first crystal 502 is placed in front of the second crystal 503, facing the incident laser beam B1 emerging from the scanner amplifier. The portion of the laser beam B1 converted into the second harmonic wavelength of about 390–430 nm after passing through the first crystal 502 is then incident upon the second nonlinear crystal 503. The second crystal 503 is cut and oriented for phase matching as described above for the second wavelength converter 110, resulting in another step of second harmonic conversion, now using the 390–430 nm beam from the first crystal 502 as the fundamental wave.

In the configuration shown in FIG. 5B, the second crystal 503 is placed in front of the first crystal 502. However, in FIG. 5B, the incident laser beam B1 passes through the second crystal 503 with practically no conversion, since the crystal is oriented for phase matching for the 390–430 nm laser pulses emerging from the first crystal 502 after the pulses reflect off of the reflective mirror 504. Thus, the portion of the laser beam B1 converted into the second harmonic wavelength of about 390–430 nm after passing through the first crystal 502 is reflected and then incident upon the second nonlinear crystal 503. The second crystal 503 is cut and oriented for phase matching as described above for the second wavelength converter 110, resulting in another step of second harmonic conversion, now using the 390–430 nm beam from the first crystal 502 as the fundamental wave.

Other modifications are necessary for optimal operation of such a one-step wave converter. For the optical arrangement shown in FIG. 5A, lens B is properly coated for maximum transmission (anti-reflection) at the 200 nm range. The material for the lens is preferably UV quartz for good optical transmission. In FIG. 5B, the modification is that the coating characteristics of the dielectric mirror 506 be highly reflective at about 198–215 nm at a 45° incident angle. These improvements for optical transmission for lens B in FIG. 5A also apply to lens A in FIG. 5B.

In the foregoing discussion, a laser fundamental wavelength range of about 790–860 nm is illustrated for a Ti-doped $Al_2O_3$ laser. However, a Ti:$Al_2O_3$ laser has an operating range of about 680 nm to about 1200 nm. Therefore, the wavelength conversion apparatus and method described above can be applied to generate a slightly extended output wavelength range of about 396–600 nm after the first conversion, and about 198–300 nm after the second conversion, without loss of generality (the lower limits are about 396 nm and 198 nm, respectively, rather than about 340 nm and 170 nm, because of limitations of the nonlinear conversion crystal 502).

In an alternative embodiment, the wavelength conversion apparatus and method may include sum frequency generation with two different laser wavelengths. In this case, the first wavelength converter 108 is structurally as described above. If the fundamental wavelength is selected to be about 790–900 nm, those wavelengths can be used to mix with the second harmonic wave of about 395–450 nm. However, the nonlinear optical crystal 502 in the second wavelength converter 110 has to be cut and oriented for phase matching conditions for the fundamental and the second harmonic waves in order to generate a laser wavelength of about 263–300 nm. If the fundamental laser wavelength from the laser unit 100 is in the range of about 790–900 nm, the laser wavelength at the output of the first wavelength converter 108 is modified by the wave mixing action of the second wavelength converter 110 to about 263–300 nm.

Operation of the Inventive Apparatus

Figure 8:
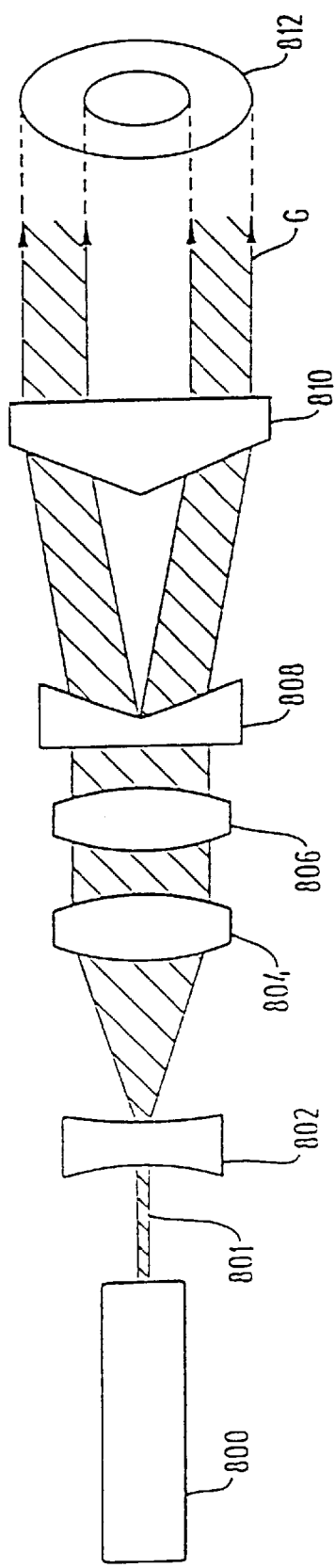
FIG. 8 is a block diagram of a guide beam unit in accordance with the present invention.

In order to improve the ease of use of the present invention, and to ensure proper alignment of the surgical laser beam S with respect to a target cornea, the present invention includes a guide beam unit 132 (see FIG. 1). The guide beam unit 132 is illustrated in greater detail in FIG. 8.

The guide beam unit 132 includes a low-power laser 800 with an output of preferably less than 1 milliwatt at initial output and preferably attenuated to the microwatt level for safe usage for direct viewing. The laser 800 in the guide beam unit 132 may be, for example, a HeNe laser or a semiconductor diode laser. The laser 800 generates a guide beam 801 which is conditioned optically so that it can be used as a indicator of the location of the surgical laser beam S. Additionally, the guide beam 801 can be used as an element for the alignment of the eye in preparation for surgical procedures.

After emerging from the laser 800, the guide beam 801 the diameter of the guide beam 801 is expanded through a telescopic beam magnifier consisting of divergent lens 802 and a convergent lens 804 to about 10 mm. The collimated beam is then compressed by a weakly focussing lens 806, with a focal length of over 500 mm, at a distance of approximately the location of the patient's cornea. An axicon first and second prism pair 808, 810 are aligned with the expanded beam such that a divergent ring image with uniform intensity is produced after the first prism 808. The second prism 810 intercept the divergent ring and diffracts it to form a ring image 812 without divergence. The diameter of the ring image is controlled by the separation between the prism pair 808, 810: the farther they are separated, the larger is the ring. The position of the second prism 810 can be adjusted by a manual or motorized drive. The guide beam 801 emerges from the guide beam unit 132 and is denoted as beam G in FIG. 1.

The ring-shaped guide beam G from the guide beam laser unit 132 is aimed at a partially transmissive mirror 134 arranged so that the reflected guide beam G is coaxial with the un-deflected surgical laser beam S. In operation, a surgeon would move the patient's head and target eye until the guide beam G is roughly centered over the patient's cornea. The surgeon will then adjust the diameter of the ring image projected on to the patient's pupil, such that the ring diameter is only slightly less than the patient's pupil size. At that point, the patient will see the guide beam G, but not necessarily at a centered position.

The patient is preferably situated in a relaxed position (e.g., supine), but with his or her head fixed within a cradle or fixture. Either the cradle or the entire operating table or chair is configured to be adjustable in fine increments about an X-Y plane perpendicular to the surgical laser beam S. The patient would then make fine adjustments of his or her own eye position with respect to the guide beam G by moving an actuator-control mechanism (e.g., a joy stick) for the cradle or operating table or chair, until the patient determines that the guide beam G appears to be at its brightest. At the completion of the patient's adjustment, the patient's eye is aligned with the patient's visual axis, coinciding with the guide beam G.

An advantage of the ring-shaped guide beam G of the present invention over a solid beam is that the fight fall-off, or decrease in brightness, is greater for the ring-shaped beam than for the solid beam when either beam is not aligned with the patient's visual axis. Thus, the ring-shaped beam provides greater visual cues to the patient when the beam is off-axis.

After the eye of the patient has been aligned using the guide beam G, the surgeon may place a suction ring 400 over the patient's eye to immobilize it. The eye tracking system 130 is then activated to compensate for any subsequent motion of the eye. With the eye immobilized, the surgeon may then commence ablative surgery using the inventive laser system.

To determine the location of each area to ablate, and the depth of ablation required, an automatic feed-back control system may be used with the inventive system. Such a control system preferably includes a corneal profiler 136 which provides information to the computer control unit 114 sufficient to determine the necessary intensity and XY-scanning coordinates for the surgical laser beam S, and to otherwise control the delivery of pulses of laser energy to the cornea, in order to achieve a desired corneal surface profile. A suitable corneal profiler 136 is any device that measures the shape or an optical property of the eye so as to provide such information.

As an alternative to a single profile measurement and ablation of the cornea based on indicated parameters, a desired corneal surface profile may be obtained through ablation by a successive approximation technique. In this technique, a measuring device is used to determine the change desired to be made in the profile of the corneal surface. Pulses of laser energy are delivered to the surface so as to bring about slightly less than the desired degree of alteration. The measuring device is then used again to determine the correction now needed to reach the desired profile. Further pulses of laser energy are provided accordingly to produce slightly less than the total calculated correction. This process is repeated until the ablated surface acquires the desired profile to a suitable degree of accuracy.

Measurement devices suitable for the corneal profiler 136 are keratometers, which are known and commercially available. Examples of such devices are the "Photokeratoscope" manufacture by the Sun Contact Lens Company of Kyoto, Japan, and the "Corneascope" manufactured by International Diagnostic Instruments, Ltd., Broken Arrow, Okla., USA. (See also S. D. Klyce, "Computer Assisted Corneal Topography", Invest. Ophthalmol. Vis. Sci. 25:1426–1435, 1984 for a comparison of these instruments and a method of using the "Photo-keratoscope"). These devices work by imaging patterns, usually concentric rings, on the corneal surface. Preferably, the keratometer used as the corneal profiler 136 in the present method is modified slightly to increase the number of lines imaged on the central portion of the cornea, thus increasing the measurement resolution of the curvature of the central portion.

In the preferred embodiment, the corneal profiler 136 receives a reflected image of a target cornea by means of a mirror 138, which is movable between an out-of-line position A and an in-line position B. When the mirror 138 is in position B, an initial profile of the cornea can be determined by the corneal profiler 136. The output of the corneal profiler 136 is coupled to the computer control unit 114, and displayed to a surgeon. In response to any resulting input from the surgeon, such as the desired final shape of the corneal surface, the computer control unit 114 determines the necessary settings and parameters, including pulse intensity, beam diameter, and target locations on the cornea, for the inventive laser system to create the desired ablation profile. The mirror 138 is then moved to position A, and the surgery commenced.

If the successive approximation technique described above is used, the mirror 138 is periodically moved back into position B, the corneal profile is re-measured, the computer control unit 114 resets the laser system, the mirror 138 is retracted to position A, and the surgery recommenced.

In determining the necessary settings and parameters, including pulse intensity, beam diameter, and target locations on the cornea, for the inventive laser system to create the desired ablation profile, the computer control unit 114 essentially prepares a three-dimensional contour map of the difference between (1) the cornea profile as measured and (2) the desired final shape of the cornea. Each point in this contour map may be described in terms of rectangular or polar coordinates, in known fashion. Starting with a selected pulse etch profile (i.e., a selected beam intensity and intensity profile), the etch depth of each pulse will be known (such information can be determined in advance by calibrating sets of profiles on corneal tissue). With a preselected etch depth, the contour map can be divided into a plurality of etch levels (for example, of the type shown in FIG. 7B). Then, using a selected initial laser pulse diameter, each level of the contour map may be characterized in terms of the X-Y coordinates of a first level pattern of etch profiles of that diameter.

For example, if the area to be ablated has a maximum diameter of 8 mm, and the laser pulse diameter is about 0.1 mm, then a grid of 80×80 pulses will cover the entire maximum diameter. Arbitrarily selecting a single origin for such a grid means that each point on a level of the contour map can be defined in terms of X-Y coordinates. As the levels become smaller in size, the laser pulse diameter may be reduced accordingly, but the principal of mapping each level of the contour map to a grid of X-Y coordinates remains the same.

Structure of the Scanner-Amplifier Laser Unit

This part of the disclosure is directed to a laser amplifier system utilizing a pair of scanning mirrors driven in tandem by piezo actuators. A control system is provided to direct a low-power laser beam while the beam is trapped and circulates between the pair of scanning mirrors. Each bounce of the laser beam between the mirrors discretely increases the power of the beam and changes the angle of exit of the beam from the amplifier, providing for precise angular beam exit control in two dimensions.

In the preferred embodiment, a laser scanner-amplifier system 8 with Ti-doped sapphire $Al_2O_3$ is used as the laser medium. However, the laser medium can be other tunable solid state laser materials, such as alexandrite, emerald, Cr:LiCaF, Cr:LiSrF, Cr:forsterite, color center lasers, or rare earth ion laser media, such as Nd, Pr, Er, Tm, Ho, or other transition metal ions such as Co, Ni in various solid state crystal hosts, including oxides or fluorides.

Figure 11:
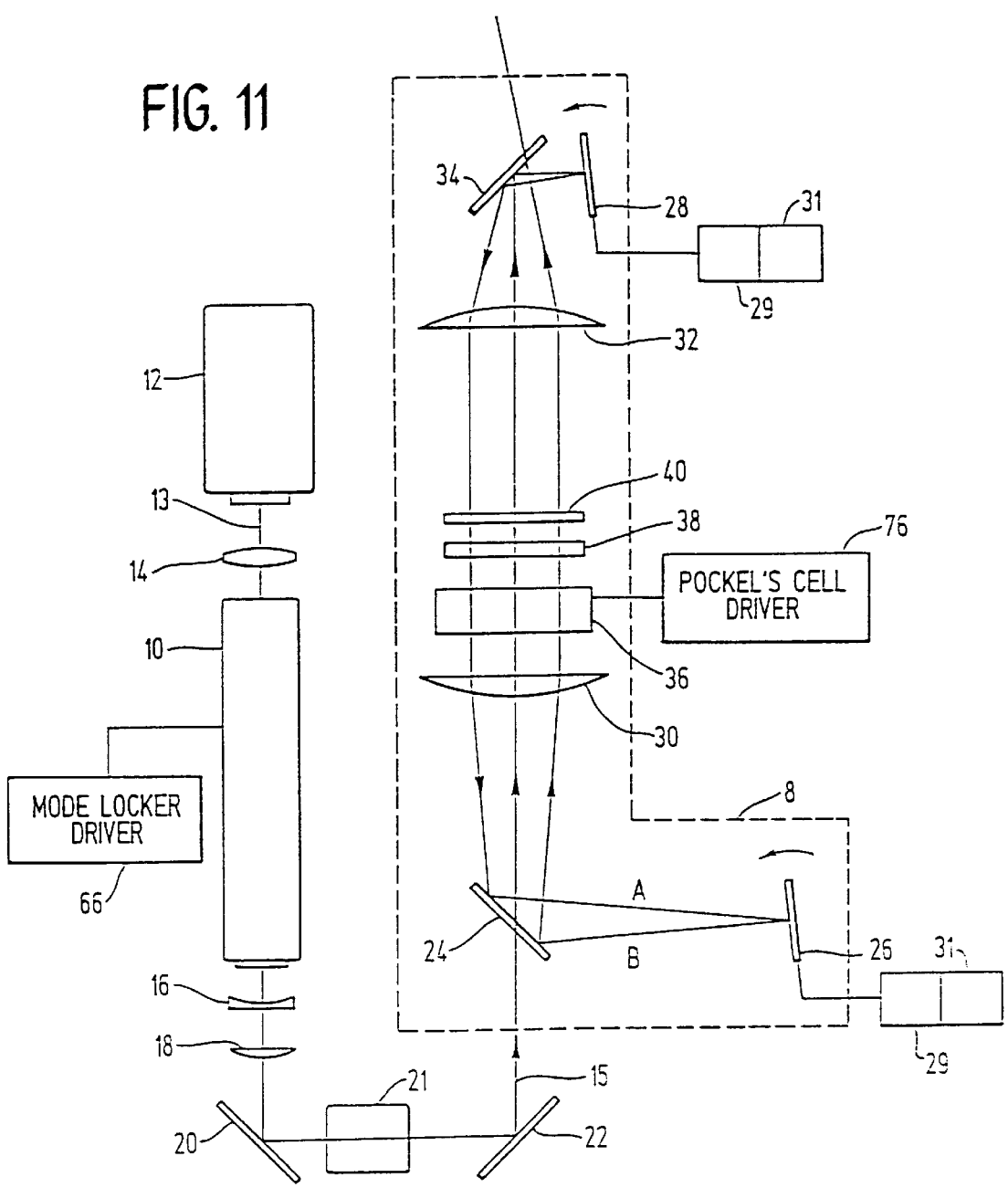
FIG. 11 is a schematic diagram of the integrated scanner-amplifier unit, consisting of a series of intra-cavity optical elements.

A laser pulse train from a mode-locked Ti-doped $Al_2O_3$ laser 10 in FIG. 11 is to be used as a seeder to the amplifier scanner system. The laser pulse frequency of the mode-locked laser, as is well known in the art, can be controlled by the round trip time of the laser pulse inside the mode-locked laser, and is at twice the driver frequency of the electrical signal applied to the mode-locked crystal. The frequency is chosen such that time period between adjacent pulses bears a preferred relationship with the arrangements of the optical elements inside the scanner-amplifier system. In the case of Ti-doped $Al_2O_3$, a continuous wave laser 12 such as, but not limited to, an argon gas laser operating at 514.5 nm or a frequency-doubled YAG or YLF laser at 532 nm and 527 nm respectively, can be used as the pump source. The pump laser beam 13 is focused into the mode-locked laser medium with a convergent lens 14. The arrangement of a laser-pumped mode-locked laser is well known in the art and a commercial model is available from Spectra-Physics, Mountain View, Calif.

The mode-locked laser beam 15 passes through a set of beam conditioning optics 16, 18. In FIG. 11, the beam cross-section is expanded by a negative (concave) lens 16 and a positive (convex) lens 18 with their focuses coinciding to form an expansion telescope. The expansion ratio can vary from 2 to 10 by choosing the appropriate focal lengths of the optical elements 16 and 18, and is determined by the mode-matching requirement between the seed beam 15 and the spatial mode of the amplifier cavity. By centering the lenses along the laser beam, minimum beam distortion and good beam collimation can be achieved as the seed beam 15 exits the optical element 18.

The seed beam is directed by high reflective mirrors 20 and 22 into the amplifier cavity. The beam first enters the cavity through a dielectric coated mirror 24 which has the optical characteristics that a pi-polarized laser beam with the electric field vector horizontal to the plane of incidence has over 96% transmission, and a pi-polarized laser beam with the electric field vector vertical to the plane of incidence has over 99% reflectability. Such thin-film polarizer elements are supplied by Burleigh NorthWest, Fishers, N.Y. The scanner-amplifier cavity 8 is confined between the scanner mirrors 26 and 28, both of which are highly reflective mirrors. The scanner mirrors 26, 28 are each mounted on a gimbal mount 29 with 90° tilts in both the horizontal and the vertical (X-Y) directions. The design of the gimbal mount can be illustrated as a mirror mount model number MM-1 manufactured and supplied by the Newport Corporation, Fountain Valley, Calif., with appropriate modifications to shorten the pivot point distance and increase the spring force. The X-Y tilts are achieved by piezoelectric actuators 31 with a material such as PZT which can have a linear travel of 40 microns of full scan range at about 1000 Hz, and at higher frequencies with smaller travel range. Such piezo actuators are supplied by a number of suppliers, including Burleigh Instruments, Fishers, N.Y. The scan mirrors 26 and 28 are driven in the same direction at the same angular degree either independently or in tandem in both the X and Y directions.

The operating characteristics of the piezo actuators may have small variations. The overall scan angles of the laser beam as emerged from the scanner-amplifier is to be calibrated against the voltage applied to the piezo actuators 31, taking into the account the small amount of hysteresis from the piezoelectric effect.

A pair of concave lenses 30 and 32 are included inside the scanner-amplifier cavity. The focal lengths of the lenses 30 and 32 are such that the focal length of lens 30 is chosen to be as large as possible, yet the size of scanner-amplifier is to be practical and convenient for use, and the focal length of lens 32 will be as short as possible, yet not so short as to cause optical break-down at its focal point. The relative locations of the lenses 30, 32 and end mirrors 26 and 28 are such that the mirrors 26 and 28 are to be at the focal point of the lenses 30 and 32, respectively, and the separation between the lenses is to be the sum of their focal lengths.

Another dielectric-coated mirror 34, which has similar characteristics as mirror 24, is used as a turning mirror and also as an exit mirror where the laser beam 15, intensity amplified and scan-angle amplified, emerges from the scanner-amplifier unit 8.

Other control elements inside the cavity include a Pockels cell 36 which consists of $LiNbO_3$ or other electro-optical crystal such as KDP. Pockels cells are commercially available from several sources, one such source is Medox Electro-optics, of Ann Arbor, Mich. With the application of electric voltage across the electro-optical crystal, a half-wave retardation in the electric field vector of the laser beam can be generated, which turns the linear polarization of a laser beam traversing the crystal, from a horizontal polarization to vertical, and vice versa. A half-wave retardation plate 38, placed next to the Pockels cell 36, is for adjusting the polarization of the beam before it reaches the mirror 34, so that the beam will either stay inside the cavity or exit the cavity at mirror 34.

A thin etalon 40 with partial reflective coating on both faces at the laser wavelength is for controlling the gain bandwidth of the seed beam 13. By choosing the appropriate finesse of the etalon, the wavelength width of the laser beam is reduced accordingly, compared to the seed beam bandwidth. The pulse duration is lengthened due to the reduced spectral content in the laser pulse.

Another method of expanding the pulse duration can be achieved by stretching the pulse spatially with an optical grating, before the pulse is injected into the beam path at location 21 shown in drawing FIG. 11. For shorter pulses, a commercial pulse compressor unit, consisting basically of a single-mode fiber and grating pair, can be placed at location 21 instead of just the optical grating. Such a unit is manufactured by Spectra-Physics Lasers, Mountain View, Calif.

Hence, the output laser pulse can be varied from a minimum which is that of the seed pulse, which is about 1 picosecond in the case of $Ti:Al_2O_3$ as the laser medium in the mode-locked laser, to as much as several hundred picoseconds.

Figure 11A:
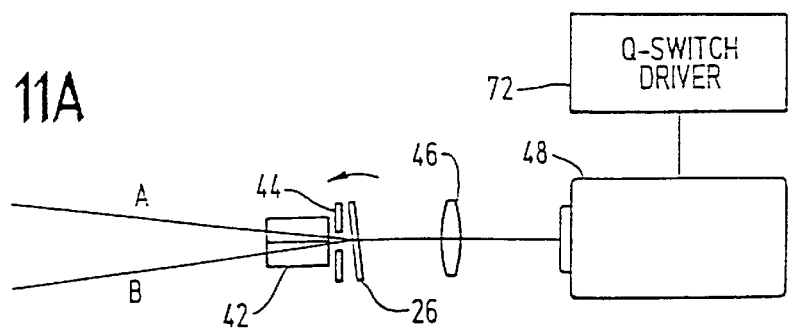
FIG. 11A is an alternative scanner-amplifier unit.

Referring now to FIG. 11A, in a second embodiment, a laser gain medium 42 is located near the scanner mirror 26. A cavity aperture 44 which has a fixed or adjustable iris with two translational degrees of freedom for proper centering with the fundamental laser mode is located inside the cavity. The laser media is optically pumped by a laser source 48 which will be described hereinafter in more detail. The second embodiment provides enhancement of the laser beam intensity inside the scanner cavity, such that the beam intensity increases by extracting energy stored in the gain medium 42.

Operation of the Preferred Scanner-Amplifier Laser Unit

For the purposes of illustration, an angle is being scanned in the horizontal plane (the X-plane). A scan voltage is applied to both piezo actuators 31 for positioning the gimbal mirror mounts for scan mirrors 26 and 28 in the same direction to the same degree; as an example, both pushing the mirrors forward as shown in FIG. 11. A half-wave voltage- electrical wave form signal is applied to the Pockels cell, as illustrated in FIG. 12B. The time sequence from 2(i) to 2(vi) marks the time development of the optical retardation of the Pockels cell 36. A voltage is to start at time 2(ii), and the optical retardation reaches half-wave at time 2(iii). The voltage is turned off at time 2(iv), and zero retardation is reached at time 2(v). The time duration between 2(ii) and 2(iii) is referred to as the rise time of the Pockels cell for a half-wave retardation. The duration between 2(iv) and 2(v) is the fall time for the same.

Since the seed laser pulse is in the picosecond range, the spatial extent of the laser energy is localized in the range of millimeters. The cavity distance between scan mirrors 26 and 28 is, for practical purpose, in the range of tens of centimeters to tens of meters. Therefore, for all practical purpose, the laser pulse can be considered localized and is represented by markers 2(i) to 2(vi) as it travels through the scanner-amplifier cavity. The seed laser beam, at time 2(i) travels towards the scanner-amplifier cavity, and enters through the thin film polarizer mirror 24. As illustrated in FIG. 12A, the beam 15 has a linear polarization with the electric field vector in the horizontal direction, as indicated by the arrow. The beam passes through the lens 30, and is focussed at a point before lens 32 which collimates the beam due to the confocal arrangement of the lenses 30 and 32 The Pockels cell (PC) voltage is at the zero level, and the polarization of the seed beam is not changed. The Pockels cell voltage then turns on at time 2(ii), right after the laser pulse exits the PC crystal. The polarization changes by 90° after passing through the half-wave plate 38, and is now vertical, as indicated by a small circle on the beam path. The beam is then reflected by the thin film polarizer mirror 34 directing the beam towards the scan mirror 28.

In FIG. 13, the beam path and the angle of incidence at mirrors 26 and 28 are illustrated. Assume that a voltage $V_1$ is applied to the piezo actuator 31, which induces a scan angle of $\theta_1$ from its zero degree incidence, at which the mirror is at the normal incidence with the incoming seed beam. The reflected beam is at an angle, 2 times $\theta_1$ from the incoming beam. Referring again to drawing FIG. 12A, the beam is reflected at mirror 28. The vertical polarization of the beam changes by 90° after passing through the half-wave plate 38. The PC voltage reaches half-wave retardation at 2(iii) (see FIG. 12B) before the laser pulse reaches the PC. On passing the PC, the polarization is rotated 90° and is now vertical. The lens 30 re-collimates the laser beam 15 and the thin film polarizer 24 is now at high reflection with respect to the vertically polarized beam. The beam 15 then travels towards the laser gain medium 42 and the cavity aperture 44.

Assuming that a voltage $V_2$ is applied to the actuator 31 in the mirror gimbal mount 29 for the scan mirror 26, an angle rotation of $\theta_2$ from the normal incidence results in the X-plane, where the normal incidence is defined as the scan mirror angular position for both mirrors 26 and 28 at which the seed laser beam 2(i) will retrace its beam path after reflection from both these mirrors. The reflected beam is, therefore, at a larger angle than the incident angle before impinging on the mirror 26, by an angle 2 time $\theta_2$, as shown in FIG. 13.

For ease of explanation, the following discussion is directed to ejecting the laser beam after only one reflection from each of the mirrors 26 and 28; however it should be understood that it is contemplated that a plurality of reflections occur from each mirror within the device prior to the beam exiting therefrom. By so choosing, the PC voltage turn-off starts after the beam emerges from the PC at time 2(iv), and the retardation is zero at 2(v) before the beam reaches the PC on its return trip from the scan mirror 26. The vertical polarization remains vertical after passing the PC, and is rotated to horizontal after the half-wave plate 38. The thin film polarized mirror is now transmissive for the laser beam, and the laser beam emerges from the amplifier-scanner of the invention with a scan angle resulting from the sum of the effects of the scan angles $\theta_1$ and $\theta_2$ from the scan mirrors 28 and 26 respectively.

It should be understood that invention makes use of the scan mirrors 26 and 28 repeatedly for one or more round trips of the beam inside the cavity to amplify and precisely direct the beam angle before exiting mirror 34.

In our preferred embodiment, the PC voltage turn-off, at times 2(iv)–2(v), is to be applied at the last leg after one or more round trips between the two scan mirrors 26 and 28. In the case where the voltage turn-off is postponed, as in the illustration in FIG. 12A, the polarization of the reflected beam from mirror 26 is rotated to horizontal after the PC, which is still at its half-wave voltage, and back to be vertical again after the half-wave plate 38. Therefore, the mirror 34 is highly reflective. The beam is trapped inside the cavity, and the beam angle increases with each reflection with either of the scan mirrors.

Further, in addition to changing the beam angle, the optical arrangement enhances the overall scan angle of the beam with a power multiplying enhancement factor.

If the focal length of the lens 30 is longer than that of lens 32, by a factor M, then:

$$M = f_{(30)}/f_{(32)}$$

where $f_{(30)}$, $f_{(32)}$ are the focal lengths of the lenses 30 and 32, respectively. The angle of incidence on mirror 28 is $\theta_1$, and the angle of incidence on mirror 26 is:

$$\theta_1/M + \theta_2.$$

Notice the angle reduction of $\theta_1$ due to the difference in the focal length of the lenses.

On passing through the lenses system from 30 to 32, the reverse, i.e., a magnification of the effective angle, occurs. The incident angle on mirror 28 is now: $(\theta_1/M + \theta_2) \times M + \theta_1$.

In the illustration in FIG. 12A, in which the laser beam is to exit the cavity after one reflection from mirrors 26 and 28, the output beam would have a scan angle of: $2 \times (\theta_1 + M \times \theta_2)$.

Notice that the scan angle due to mirror 26, $\theta_2$, is magnified by a factor M.

If a total of N reflections are allowed to occur for each of the two scan mirrors, the final scan angle of the exit beam is: $2N \times (\theta_1 + M \times \theta_2)$.

Since each reflection or transmission on an optical surface causes a certain amount of intensity loss and optical distortion in the laser beam, ideally the intended scan angle will be achieved with the smallest number of optical surface contacts. If the scan mirrors have identical gimbal mounts 29 and piezo actuators 31, the mirrors can be scanned in tandem, and $\theta_1$ and $\theta_2$ will be substantially equal. The optical loss due to scattering from all the optical elements inside the cavity is reduced by the factor: $(M+1)/2$ For M=3, and 10 round trips inside the cavity, the scan angle is amplified by 20 times more than the amplification of the scan angles from two like but uncoupled piezo mirrors.

It is also clear that all the foregoing discussion about scanning in the horizontal direction is also applicable to the vertical direction (a Y-scan), by applying the scan voltage to the piezo actuator which controls the vertical tilt of the scan mirror. By applying the appropriate voltages to the actuators controlling the horizontal and the vertical scan directions, the laser beam can be directed to any predetermined location in the two dimensional angular space.

The pump source 48 of the Ti:Al$_2$O$_3$ in the amplifier cavity in FIG. 11A consists of two major components, namely, a Nd-doped YAG or YLF laser which is continuously pumped by arc lamps such as Kr or Ar gas lamp, which is supplied by ILC Technology, Sunnyvale, Calif., or by semiconductor diode arrays with the emission laser wavelength to match the absorption band of Nd-doped YAG or YLF. Several hundred to over one thousand watts of continuous wave laser output power from Nd:YAG is attainable with multiple lamp-pumped laser heads inside a laser cavity. Such lasers are supplied by Lasermetric, Orlando, Fla., and a number of other industrial YAG laser suppliers.

In a preferred embodiment, the Ti ion has an absorption band centered at about 520 nm, with a full width at half maximum of about 100 nm. The second harmonic wavelengths of the Nd-doped YAG and YLF are centered around 532 nm and 527 nm, respectively, and both are suitable as a pump source.

In the second harmonic generation (SHG) process, one of limiting factors in the conversion efficiency and the power stability is the temperature gradient induced by absorption of the laser at its fundamental and second harmonic frequency. Choosing a second harmonic crystal with good thermal conductivity, and cooling the crystal by liquid flow or by contact cooling, are among the common methods to extend the upper limit of the input fundamental laser power for the SHG crystal.

Figure 14A:
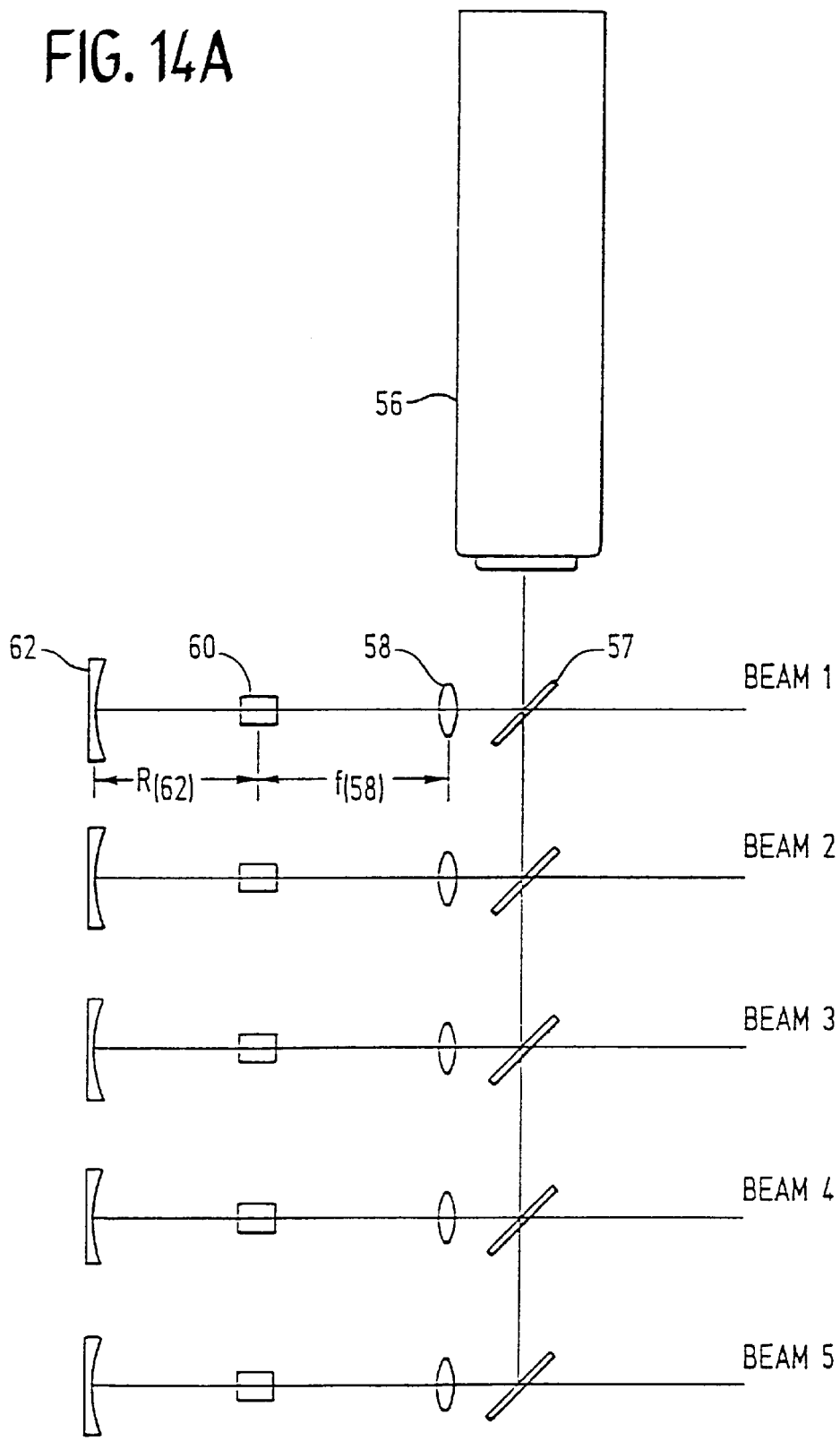
FIG. 14A is a schematic showing a means of generating stable second harmonic laser power.
Figure 14B:
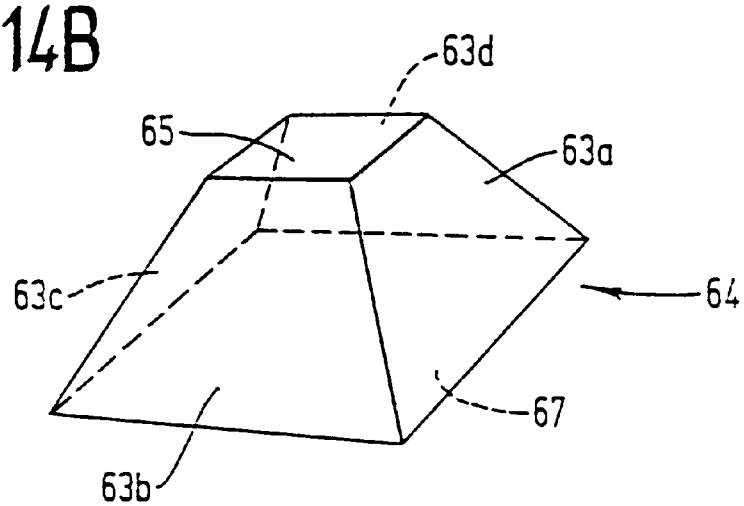
FIG. 14B is a perspective showing of a spatial combiner for combining the plurality of pump beams of FIG. 14A.
Figure 14C:
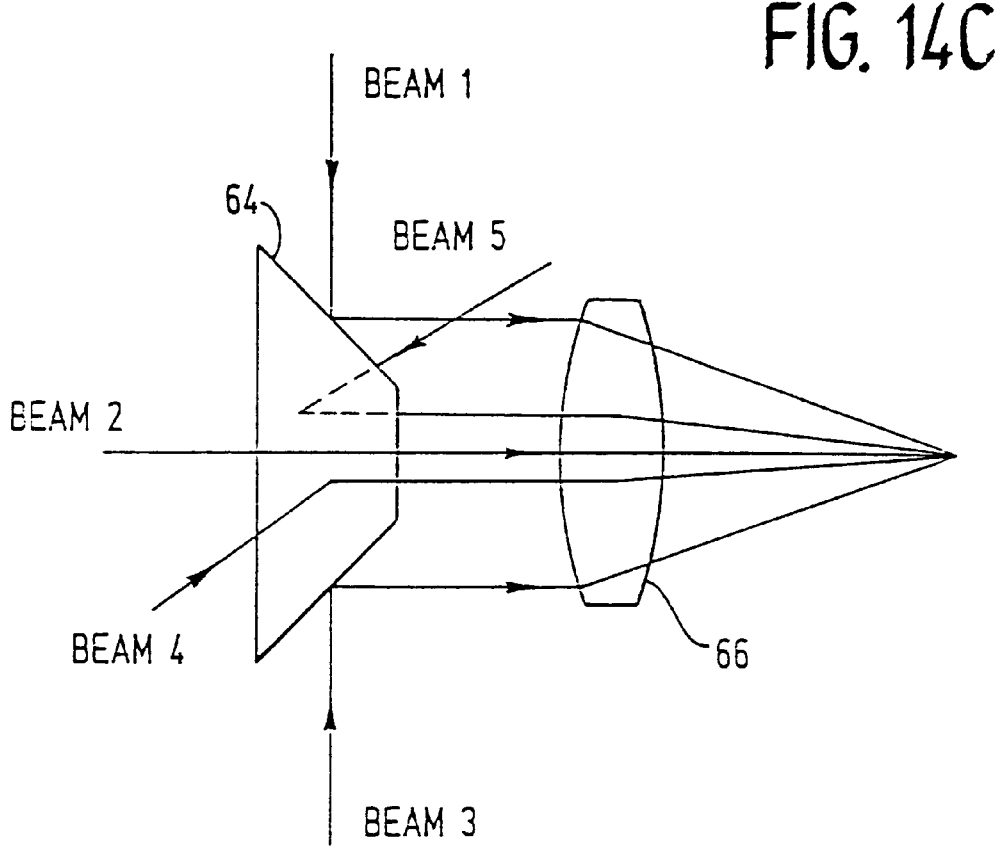
FIG. 14C schematically depicts the combining of the beams of FIG. 14A into a single second harmonic beam from the generated beam of FIG. 14A.

Referring now to drawing FIGS. 14A, 14B and 14C, the output laser beam 55 of a high power, acoustic-optical switched, Nd-doped YAG or YLF laser beam source 56 is directed to a series of partially reflecting beam splitters 57, which are coated with dielectric so that, at the 45° incidence, they all have high transmission for the second harmonic wavelength, and each succeeding splitter is highly reflective at the fundamental wavelength of the laser source 56, so that the laser beam power is distributed equally among each branch when they are directed towards the SHG crystals 60. The crystal 60 is chosen for high nonlinear coefficient, good acceptance angle, and high tolerance to a temperature gradient KTP is among the top choices as a SHG crystal for conversion at 1.04 to 1.06 microns.

In a preferred embodiment, 20–60 watts of average power will be achieved in the beams 1–5 of FIG. 14A. To further increase the conversion efficiency, a convex lens 58 can be inserted between each splitter 57 and each SHG crystal 60, such that the crystal is at the focal distance $f_{(58)}$ from the lens, where the beam cross-section is the smallest and the laser power density is the highest. The focal length of the lens is chosen to optimize for the acceptance angle of the SHG crystal. A spherical concave mirror 62 that is highly reflective at both the fundamental and the second harmonic wavelength is placed at the radius of curvature of the mirror 62, $R_{(62)}$, from the first surface of the crystal, where the laser beam enters the crystal. This optical arrangement allows for the return beams of both the fundamental and the second harmonic to retrace the beam path of their first passage in the crystal, and ensure a good beam overlapping in the crystal even though there may be walk-off between the beams after their first pass.

To illustrate our embodiment, we combine five beams at the second harmonic wavelength with a novel spatial combiner 64. As shown in FIG. 14B, the combiner 64 is a six-face optical element which has four sides 63a, 63b, 63c and 63d, each of which form a 45° angle with the base face 67, and a top face 65 which is parallel to its bottom face 67. The side faces are coated for high reflectivity at 45° at the second harmonic wavelength, and the top and bottom faces are coated with an anti-reflection coating at the second harmonic wave-length. As shown in FIG. 14C, by using beam steering optics, the five beams from FIG. 14A can be reflected off the side faces of the combiner 64, and one beam (beam 2) in FIG. 14C can transmit through the parallel faces. The beams are adjusted such that they re-collimated and are parallel with each other. A convex lens 66 is centered symmetrically in the beam path, and focuses the five beams into a common focal point. This optical element 66 can be a replacement of or an equivalent to the element 46 of FIG. 11.

It also follows from the present invention that additional beams can be combined with a spatial combiner with additional facets on the combiner. As an example, a hexagon, instead of a square top, can combine up to 7 beams.

In another embodiment, the facets can be formed on more than one layer, such as 4 facets on the top tier and 6 facets on the second tier.

Figure 15A:
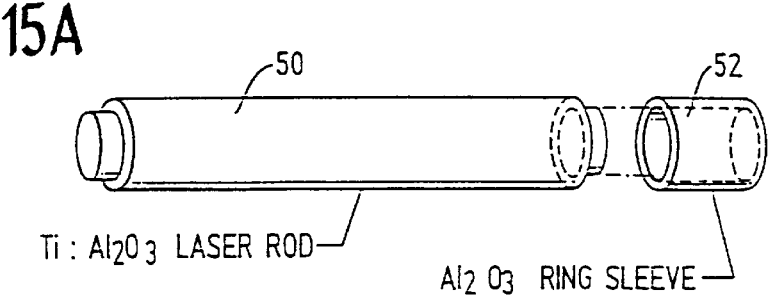
FIG. 15A is an exploded perspective view showing a method of mounting the laser medium.
Figure 15B:
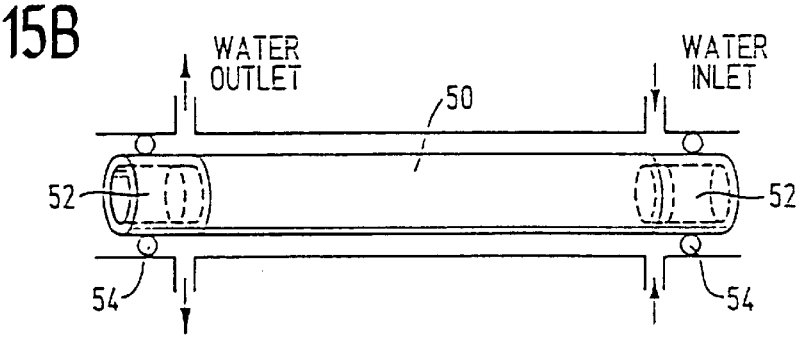
FIG. 15B is a cutaway perspective view of the laser medium of FIG. 15A enclosed in a water jacket for cooling.

In all end pumping configurations, the pump beam is absorbed by the laser active ions in the crystal host. The energy distribution in the laser medium is a negative exponential function, with a maximum at the entrant face. For efficient cooling, and to minimize the distortion of the laser beam, the laser medium in the invention is to be in a cylindrical laser rod form. A conventional laser rod is mounted with the end faces outside of the contact with the coolant. In FIG. 15A, the preferred embodiment consists of a Ti:$Al_2O_3$ laser rod with a recessed collar 50. A thin wall tube made of undoped sapphire 52 is to fit at the end sections of the laser rod. The tube piece is glued to the laser rod, and the whole has a cylindrical shape as shown in FIG. 15B. This cylindrical piece is then mounted to a liquid cooled envelope similar to the ones used in an arc lamp pumped laser. A water flow channel around the laser medium and the extension is shown in FIG. 15B, in which the water inlets and outlets are shown schematically. O-rings 54 are retained in such a manner that the coolant is sealed from coming into contact with the flat laser surfaces of the laser rods. The tube extension allows the whole laser medium to be in contact with the liquid coolant. Using the same material in the extension tube also minimizes stress as a result of a difference in thermal expansion coefficient, with temperature variation in the whole assembly.

In another embodiment, an additional pump source can be applied through mirror 24 collinear with laser path from pump source 48, such that the laser media is pumped from both ends.

In another embodiment, additional laser media is to be included in front of the scan mirror 28, and a pump configuration identical to optical elements 46 and 48, pumping one end of the laser medium, or pumping from both ends of the laser medium, is to be applied to the laser medium near mirror 28.

Figure 16:
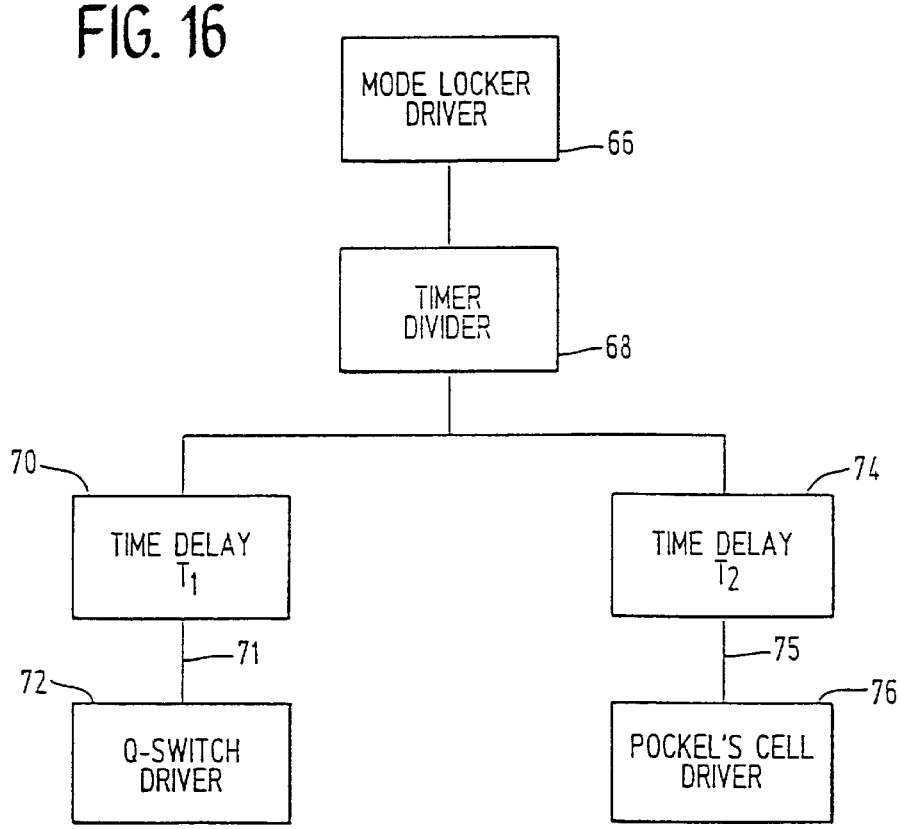
FIG. 16 is a block diagram showing the electrical connections between the mode-locked laser driver, the timer-divider circuit, the Pockels cell driver, and the Q-switch driver of the pump laser.

Multi-kilohertz laser operation is achieved with the following method. A synchronized electrical wave form is tapped from the mode locker driver 66. According to the desired repetition rate, the synchronized signal can be divided electrically by a timer divider circuit 68, as shown diagrammatically in FIG. 16. The resultant frequency output of the timer-divider determines the laser frequency of the scanner-amplifier system. The output electrical signal of the divider box is then time-delayed through delay generators 70 and 74, commercially available from Stanford Research Systems, Sunnyvale, Calif. One of the delayed signals 71 is fed into a Q-switched driver 72 in the pump laser 48, and a second time-delayed signal 75 is fed into the Pockels cell driver 76.

The timing of the electrical signals and the laser events are illustrated in FIG. 17. In the top trace FIG. 17A, multi-megahertz (30–200 MHz) mode locked laser pulses are represented by equally spaced laser spikes at time intervals equal to twice the mode locker driver frequency. After the timer-divider circuit, electrical signals at multi-kilohertz (1,000–50,000 Hz) is generated at the output of the timer-divider box, as represented by the trace FIG. 17B. At a time delay $T_1$, the Q-switch driver for the pump laser is turned on, in trace FIG. 17C, generating a short pulse of the second harmonic laser pump pulse at a time delay $T_r$, corresponding to the build up of the pump pulse, a characteristic of the pump configuration, and the gain factor at the pump laser medium. The second harmonic pump pulse is absorbed in the Ti:Al$_2$O$_3$ laser medium, in FIG. 17D. The Pockels cell is switched on at a time delay $T_2$ relative to a synchronized timer-divider signal, which is the pulse after the one that triggers the Q-switch driver. The time delay $T_2$ is determined by the actual location of the seed laser pulse from the mode locked laser, as aforementioned along with the discussion of FIG. 12A. The delay time $T_1$ is to be adjusted so that the peak of the population inversion is to occur when the Pockels cell crystal reaches the half-wave retardation point of 2(iii) as shown in FIG. 12B.

Applicable Surgical Procedures

The laser surgical system of the present invention can perform numerous types of surgical procedures on the cornea. Among other procedures, two types of laser tissue interaction are particularly suited for the inventive system:

(1) The inventive system can easily create straight line and curved-line incisions, of any predetermined length and depth, at any location determined by a surgeon.

Figure 9A:
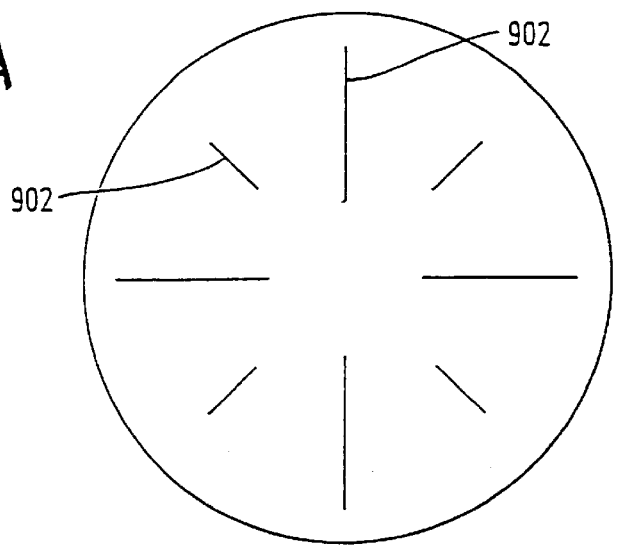
FIG. 9A is a top view of a cornea, showing the use of the present invention to make radial incisions on the cornea.

As illustrated in FIG. 9A, multiple radial cuts 902, equal or partially equal in incision length and with an angular separation between cuts, can be made on the cornea with the present surgical system. An incision can be made by directing the surgical laser beam S to a predetermined location at the cornea, and removing the desired amount of tissue by controlling the laser beam energy dosage. The present invention provides options for making an incision with either a wide incision width by using a larger beam spot size on the cornea surface, or a fine incision by using a more focussed beam spot. With the present invention, the depth of each cut can be varied over the length of the cut.

Figure 9B:
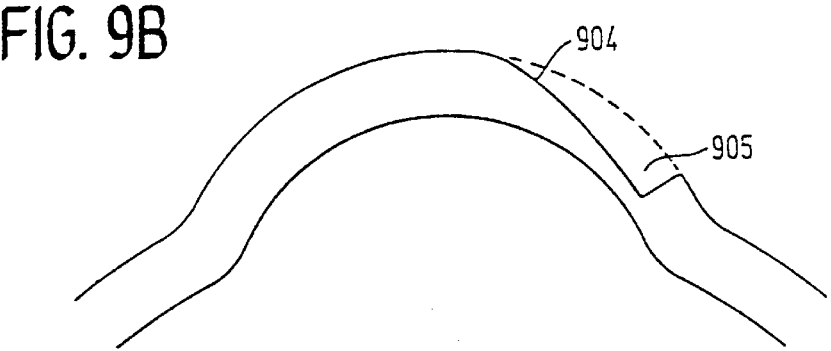
FIG. 9B is a cross-sectional side view of a cornea, showing variable-depth incisions made using the present invention.

In FIG. 9B, a side view of a cross-section of the cornea shows a shallower cut depth 904 near the central region of the cornea and a deeper cut depth 905 near the outer edge of the cornea. Such a procedure provides more uniform stretching of the cornea from the central to the edge regions, and increases visual acuity post-operatively.

Figure 9C:
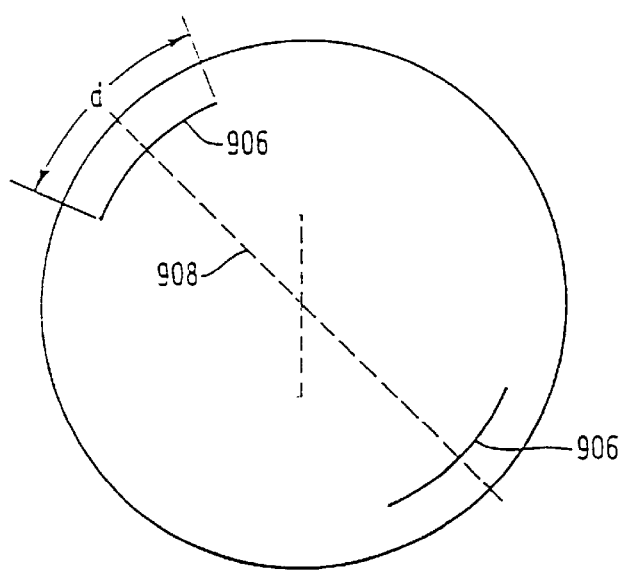
FIG. 9C is a top view of a cornea, showing the use of the present invention to make transverse-cut incisions on the cornea.

The invention can also easily generate transverse cuts ("T-cuts"), as shown in FIG. 9C. By directing the surgical laser beam S to make a pair of opposing transverse incisions 906 along an axis 908 relative to the center of the eye, the refractive power of eye is decreased along the axis. The exact length d and the location of the incision can vary according to the amount of desired correction, in known fashion.

The inventive system can also be used for procedures in cornea transplants. A circumcision of the cornea in any predetermined shape (e.g., circular, elliptical, hexagonal, etc.) can be performed on the donor eye and the recipient's eye. In both cases, the computer control unit 114 calculates the beam location based on the particular shape required, and the amount of laser energy needed to cut through the cornea.

In general, incisions in the cornea can be made at effective locations for performing radial keratotomies or making T-cuts, to correct myopia, hyperopia, or astigmatism.

(2) The second important type of laser-tissue interaction provided by the inventive system is area ablation, which permits direct sculpting of the corneal surface.

Figure 10A:
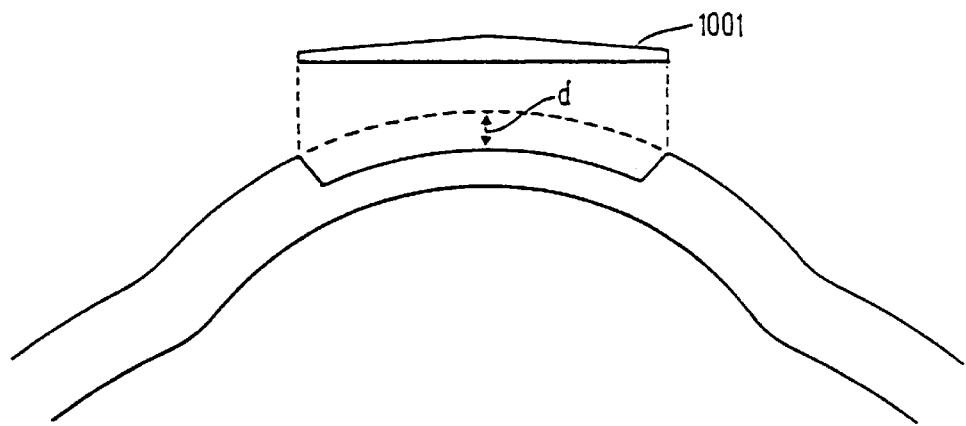
FIG. 10A is a cross-sectional side view of a cornea, showing the use of the present invention to remove tissue to a desired depth d over a predetermined area on the cornea, and showing an alternative method for performing a cornea transplant.

As illustrated in FIG. 10A, a local scar or infected tissue can be removed with the present invention. The defective tissue is removed to a desired depth d over a predetermined area on the cornea. A donor cornea cap can be cut and ablated ("sculpted") to the desired dimension and thickness using the invention. The cap piece is then transferred to the bared stroma bed and attached by suture, glue, or other appropriate means, in known fashion.

Again in FIG. 10A, an alternative method is shown for performing a cornea transplant. The invention can be used to ablate the cornea most of the way or all of the way through from the epithelium to the endothelium of the cornea. Then a donor cornea 1001 is cut to matching dimensions, and attached to the open ablated area by sutures or other known methods.

Figure 10B:
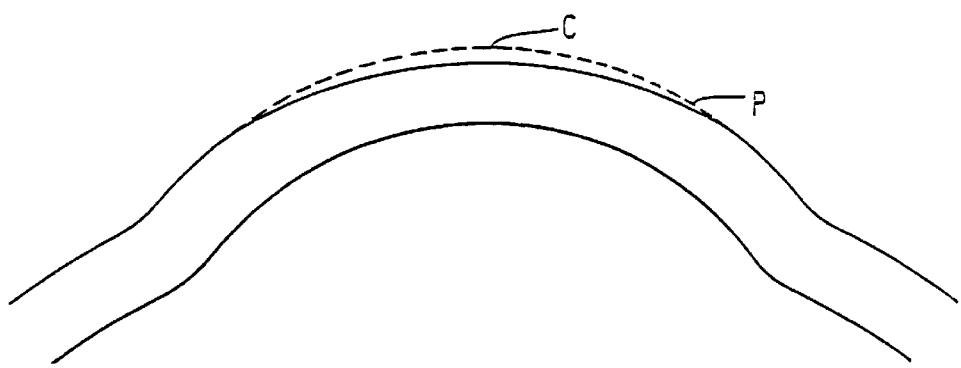
FIG. 10B is a cross-sectional side view of a cornea, showing the use of the present invention to correct myopia.

For myopia correction, as illustrated in FIG. 10B, the curvature of the cornea can be reduced by selectively ablating the cornea in such a way that more tissue is removed at the center portion C of the cornea, with a decreasing amount of tissue being removed towards the periphery P of the cornea. Prior to the laser procedure, the epithelium optionally may be removed by mechanical means. The new desired profile of the eye may include the Bowman's membrane and part of the stromal layer, depending on the amount of refractive correction required. As described earlier, the computer control unit 114 provides for the sequence, location, and intensity of laser pulses to be deposited. The deposition pattern is preferably in accordance with the patterns discussed above in the section "Method of Depositing Laser Pulses".

Figure 10C:
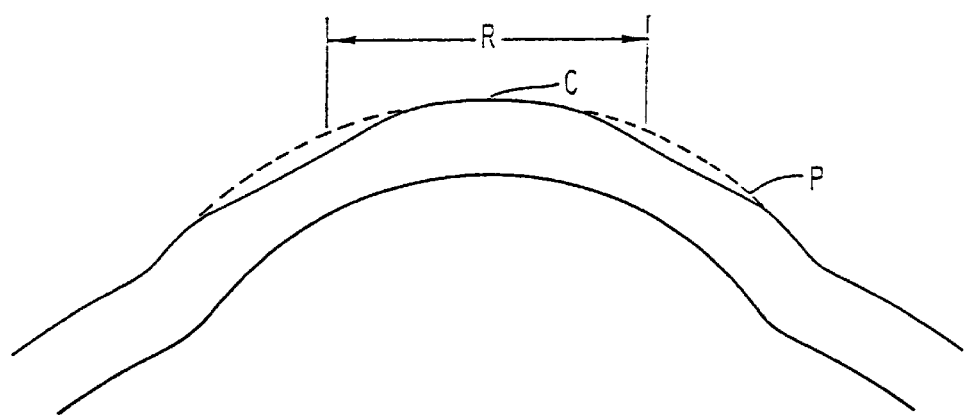
FIG. 10C is a cross-sectional side view of a cornea, showing the use of the present invention to correct hyperopia.

For hyperopia correction, as illustrated in FIG. 10C, the objective is to increase the curvature of the eye. Cornea tissue is to be removed in increasing thickness from the center portion C out towards the periphery P of the cornea. Depending on the amount of correction in the refractive power, the etch gradient for the removed tissue varies. As indicated in FIG. 10C, the depth of the removed tissue again decreases near the periphery of the eye for a smooth transition. The size of the usable central region R varies depending on the amount of hyperopic correction.

The invention is particularly useful for the correction of asymmetric refractive errors. Irregular distortions may result from poor matching of a cornea from a transplant, uneven suturing, or from imperfect refractive surgical procedures such as lamellar keratomileusis or epikeratophakia. The inventive system can direct the surgical laser beam S to any desired location to sculpt the cornea according to a predetermined shape. The surgical laser beam thus can be applied to smooth out an irregular profile.

Another use of the invention is to produce standard or custom sculpted cornea caps in advance of need. The invention can be used on a donor cornea or a synthetic cornea substitute to ablate a desired profile to correct for myopia, hyperopia, or astigmatism. Such sculpted caps can then be attached to a properly prepared cornea, in known fashion.

Summary

A number of embodiments of the present invention have been described. Nevertheless, it will be understood that various modifications may be made without departing from the spirit and scope of the invention. For example, while the invention has been described in terms of rectangular coordinates, equivalent polar coordinates may be used instead. In addition, other lasing media may be used so long as the resulting wavelength, pulse duration, and pulse repetition rate is within the corresponding ranges set forth above. Accordingly, it is to be understood that the invention is not to be limited by the specific illustrated embodiment, but only by the scope of the appended claims.

What is claimed is:

1. An eye tracking system provided within a laser surgery system for performing ophthalmic surgery, the system comprising:
   a laser source means for generating a laser beam for tissue ablation at an undeflected laser beam location;
   means for controlling laser beam location;
   indicator means for indicating location of an eye, that is adapted to be placed in contact with the eye;
   closed-loop control means that includes means for activating the eye tracking system at an initial position of the eye, and the control means uses the initial undeflected beam location as a reference location of the eye; and
   location detector means directed towards the indicator means through relay optics means to receive an image of the indicator means, and for generating a bias signal proportional to relative distance of a current image location relative to the reference location of the eye at the location detector means, such that the bias signal is adapted to indicate eye movement away from the undeflected beam location,
   wherein the closed-loop control means is coupled to the laser beam location control means and the location detector means such that a non-zero bias signal from the location detector means causes the laser beam location control means to move the laser beam's undeflected location until the location detector means determines that the image of the indicator means returns to the reference location corresponding to the bias signal being approximately zero.

2. The eye tracker system in claim 1, wherein the indicator means includes a ring providing reflective markings means on its surface facing the laser beam for indicating x and y translational axes and rotational movement of the eye.

3. The eye tracker system in claim 2, wherein the ring has an attachment means for securing to the eye.

4. The eye tracker system in claim 3, wherein the attachment means comprises a device with means for applying a suction force.

5. The eye tracker system in claim 2, wherein the marking means includes two substantially orthogonal marks tangential to the ring, to indicate the x and y translational movement of the eye, and a radial mark along the radial direction of the ring to indicate the rotational movement of the eye.

6. The eye tracker system in claim 5, wherein the location detector means comprises two linear array sensors for the x and y translation marks, and each sensor is positioned to receive the image of one of the marks and is oriented substantially orthogonal to the image orientation.

7. The eye tracker system in claim 5, wherein the location detector means further includes a third array sensor for the rotation movement of the eye, and the sensor is positioned to receive the image of the radial mark and is oriented substantially orthogonal to the image orientation.

8. The eye tracker system in claim 1, wherein the means for controlling laser beam location comprises adjustable steering mirrors responsive to the signals indicating positions of the eye.

9. The eye tracker system in claim 1, wherein the means for controlling laser beam location comprises a rotatable dove prism responsive to a signal indicating orientation of the eye.

10. The eye tracker system in claim 1, wherein the relay optics means comprises lenses and mirrors, such that the image of the marks of the indicator means is substantially focussed onto the location detector means.

* * * * *